United States Patent
Buchholz et al.

(10) Patent No.: US 9,603,367 B2
(45) Date of Patent: Mar. 28, 2017

(54) PESTICIDAL MIXTURES INCLUDING SPIROHETEROCYCLIC PYRROLIDINE DIONES

(71) Applicant: Syngenta Participations AG, Basel (CH)

(72) Inventors: Anke Buchholz, Stein (CH); Fabienne Hatt, Basel (CH); Alfred Rindlisbacher, Stein (CH); Michel Muehlebach, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/370,991

(22) PCT Filed: Jan. 17, 2013

(86) PCT No.: PCT/EP2013/050794
§ 371 (c)(1),
(2) Date: Jul. 8, 2014

(87) PCT Pub. No.: WO2013/107796
PCT Pub. Date: Jul. 25, 2013

(65) Prior Publication Data
US 2015/0031533 A1    Jan. 29, 2015

(30) Foreign Application Priority Data
Jan. 17, 2012 (EP) .................... 12151447

(51) Int. Cl.
*A01N 47/06* (2006.01)
*A01N 47/18* (2006.01)
*A01N 47/22* (2006.01)
*A01N 43/90* (2006.01)

(52) U.S. Cl.
CPC ............ *A01N 47/06* (2013.01); *A01N 43/90* (2013.01); *A01N 47/18* (2013.01)

(58) Field of Classification Search
CPC combination set(s) only.
See application file for complete search history.

(56) References Cited

U.S. PATENT DOCUMENTS

2004/0044066 A1   3/2004   Fischer
2010/0311777 A1*  12/2010  Zambach .......... A01N 43/38 514/278
2011/0301031 A1*  12/2011  Muehlebach ....... A01N 43/90 504/103

FOREIGN PATENT DOCUMENTS

| WO | 2009049851 | 4/2009 |
|---|---|---|
| WO | 2010063670 | 6/2010 |
| WO | 2010066780 | 6/2010 |
| WO | 2011151199 | 12/2011 |

OTHER PUBLICATIONS

HCAPLUS abstract 1978:100327 (1978).*
HCAPLUS abstract 1971:404564 (1971).*
International Search Report dated Aug. 7, 2013 for International Patent Application No. PCT/EP2013/050794.

* cited by examiner

Primary Examiner — John Pak
(74) Attorney, Agent, or Firm — R. Kody Jones

(57) ABSTRACT

A pesticidal mixture comprising as active ingredient a mixture of component A and component B, wherein component A is a compound of formula (I), in which Q is i or ii wherein X, Y and Z, m and n, A, G, and R, are as defined as in claim 1, and component B is a compound selected from the insecticides as defined in claim 1. The present invention also relates to methods of using said mixtures for the control of plant pests.

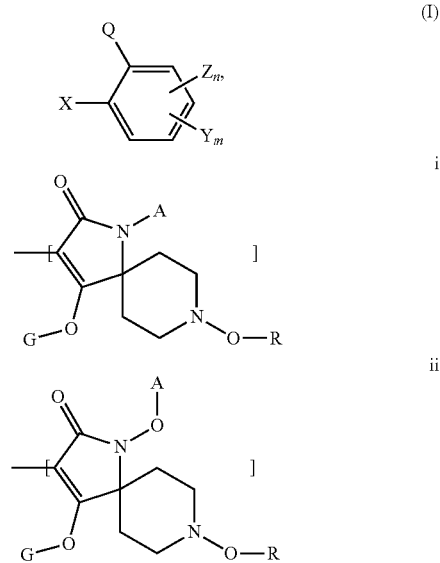

7 Claims, No Drawings

PESTICIDAL MIXTURES INCLUDING SPIROHETEROCYCLIC PYRROLIDINE DIONES

RELATED APPLICATION INFORMATION

This application is a 371 of International Application No. PCT/EP2013/050794, filed Jan. 17, 2013, which claims priority to EP Patent Application No. 12151447.5, filed Jan. 17, 2012, the contents of which are incorporated herein by reference herein.

The present invention relates to mixtures of pesticidally active ingredients and to methods of using the mixtures to control insects, acarines, nematodes or molluscs.

WO 2009/049851, WO 2010/063670 and WO10/066,780 disclose that certain spiroheterocyclic pyrrolidine diones have insecticidal activity.

The present invention provides pesticidal mixtures comprising as active ingredient a mixture of component A and component B, wherein component A is a compound of formula (I)

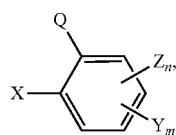

in which Q is
i or ii

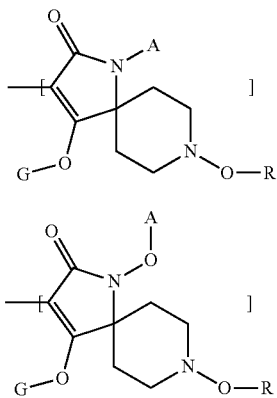

X, Y and Z independently of each other are $C_{1-4}$alkyl, $C_{1-4}$haloalkyl, $C_{1-4}$ alkoxy, $C_{1-4}$ haloalkoxy, halogen;

m and n, independently of each other, are 0, 1, 2 or 3 and m+n is 0, 1, 2 or 3;

G is hydrogen, a metal, an ammonium, a sulfonium or a latentiating group;

R is hydrogen, $C_{1-4}$alkyl, $C_{1-4}$haloalkyl;

A is hydrogen, $C_{1-4}$alkyl, $C_{1-4}$haloalkyl, $C_{2-4}$alkenyl, $C_{2-4}$haloalkenyl, $C_{1-4}$alkoxy($C_{1-4}$)alkyl, $C_{1-4}$haloalkoxy($C_{1-4}$)alkyl, $C_{1-4}$alkoxy($C_{1-4}$)alkoxy($C_{1-4}$)alkyl, tetrahydrofuranyl, tetrahydropyranyl; and or an agrochemically acceptable salt or an N-oxide thereof;

and component B is selected from at least one of:
a) Spinosad
b) Pirimicarb
c) Amitraz
d) Buprofezin
e) Pyriproxyfen
f) Triazamate
g) Chlorpyrifos
h) Isoprocarb
i) Indoxacarb
j) Metaflumizone
k) Fipronil
l) Ethiprole
m) Lufenuron
n) Profenofos
o) Oxamyl
p) Bifenthrin
q) Cyfluthrin
r) Deltamethrin
s) Tefluthrin
t) Etoxazole
u) Bifenazate
v) Tau-fluvalinate In the compounds of formula (I) of Component A, each alkyl moiety either alone or as part of a larger group is a straight or branched chain and is, for example, methyl, ethyl, n-propyl, n-butyl, iso-propyl, sec-butyl, iso-butyl, and tert-butyl.

Alkoxy groups preferably have a preferred chain length of from 1 to 4 carbon atoms. Alkoxy is, for example, methoxy, ethoxy, propoxy, iso-propoxy, n-butoxy, iso-butoxy, sec-butoxy and tert-butoxy. Such groups can be part of a larger group such as alkoxyalkyl and alkoxyalkoxyalkyl. Alkoxyalkyl groups preferably have a chain length of 1 to 4 carbon atoms. Alkoxyalkyl is, for example, methoxymethyl, methoxyethyl, ethoxymethyl, ethoxyethyl, n-propoxymethyl, n-propoxyethyl or iso-propoxymethyl.

Halogen is generally fluorine, chlorine, bromine or iodine. This also applies, correspondingly, to halogen in combination with other meanings, such as haloalkyl or haloalkoxy.

Haloalkyl and haloalkoxy groups preferably have a chain length of from 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl. Haloalkoxy is, for example, fluoromethoxy, difluoromethoxy, trifluoromethoxy, chloromethoxy, dichloromethoxy, trichloromethoxy, 2,2,2-trifluoroethoxy, 2-fluoroethoxy, 2-chloroethoxy, pentafluoroethoxy, 1,1-difluoro-2,2,2-trichloroethoxy, 2,2,3,3-tetrafluoroethoxy and 2,2,2-trichloroethoxy; preferably trichloromethoxy, difluorochloromethoxy, difluoromethoxy, trifluoromethoxy and dichlorofluoromethoxy.

The latentiating groups G are selected to allow its removal by one or a combination of biochemical, chemical or physical processes to afford compounds of formula (I) where G is hydrogen before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

Such latentiating groups are known in the art, for example, from WO08/071,405, WO09/074,314, WO09/049,851, WO10/063,670 and WO10/066,780.

In one embodiment, the latentiating group G is selected from the group —C(=O)—$R^a$ and —C(=O)—O—$R^b$; wherein $R^a$ is selected from hydrogen, $C_1$-$C_{12}$alkyl, $C_2$-$C_{12}$alkenyl, $C_2$-$C_{12}$alkynyl, $C_1$-$C_{10}$haloalkyl and $R^b$ is selected from $C_1$-$C_{12}$alkyl, $C_2$-$C_{12}$alkenyl, $C_2$-$C_{12}$alkynyl and $C_1$-$C_{10}$haloalkyl. In particular, $R^a$ and $R^b$ are selected from the group consisting of methyl, ethyl, n-propyl, iso-propyl, n-butyl, iso-butyl, sec-butyl, tert-butyl, ethenyl and propenyl, e.g. 2-propen-1-yl.

It is preferred that G is hydrogen, a metal, preferably an alkali metal or alkaline earth metal, or an ammonium or sulfonium group, where hydrogen is especially preferred. Depending on the nature of the substituents, compounds of formula (I) may exist in different isomeric forms. When G is hydrogen, for example, compounds of formula (I) may exist in different tautomeric forms:

dihexylamine, diheptylamine, dioctylamine, ethanolamine, n-propanolamine, i-propanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-i-opropylamine, tri-n-butylamine, tri-i-butylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, i-propylamine and di-1-propylamine.

Preferred quaternary ammonium bases suitable for salt formation correspond, for example, to the formula [N($R_a R_b R_c R_d$)]OH, wherein $R_a$, $R_b$, $R_c$ and $R_d$ are each indepen-

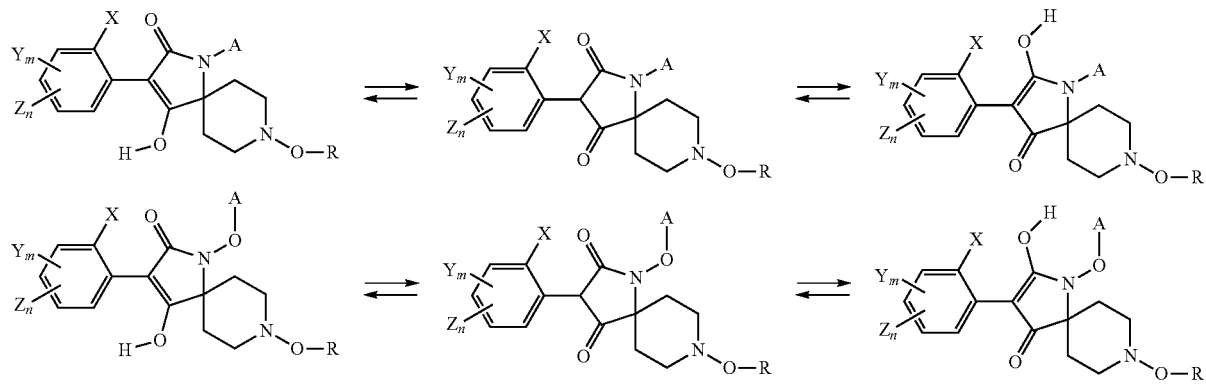

This invention covers all isomers and tautomers and mixtures thereof in all proportions. Also, when substituents contain double bonds, cis- and trans-isomers can exist. These isomers, too, are within the scope of the claimed compounds of the formula (I).

The invention relates also to the agriculturally acceptable salts which the compounds of formula (I) are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, i-propylamine, the four butylamine isomers, n-amylamine, i-amylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-i-propylamine, di-n-butylamine, di-n-amylamine, di-i-amylamine, dently of the others hydrogen or $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula [$SR_e R_f R_g$]OH, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

The compounds of the invention may be made by a variety of methods as described in detail, for example, in WO09/049,851, WO10/063,670 and WO10/066,780.

It should be understood that in those compounds of formula (I), where G is a metal, ammonium or sulfonium as mentioned above and as such represents a cation, the corresponding negative charge is largely delocalised across the O—C=C—C=O unit.

The compounds of formula (I) according to the invention also include hydrates which may be formed during the salt formation.

Preferably, in the compounds of the formula (I), the substituent R is hydrogen, $C_{1-4}$alkyl, $C_{1-4}$haloalkyl, in particular methyl, ethyl, iso-propyl, n-propyl, tert-butyl, sec-butyl, iso-butyl, or n-butyl.

Preferably, X, Y and Z, are selected, independently of one another, from $C_1$-$C_4$alkyl, $C_1$-$C_4$alkoxy or halogen, in particular methyl, ethyl, iso-propyl, n-propyl, methoxy, fluoro, bromo or chloro, when m+n is 1, 2 or 3, in particular, when m+n is 1 or 2.

Alternatively, Y and Z, independently of each other, denote $C_1$-$C_4$alkyl, $C_1$-$C_4$alkoxy, halogen, in particular methyl, ethyl, iso-propyl, n-propyl, methoxy, fluoro, chloro, bromo, when m+n is 1, 2 or 3, in particular, when m+n 1 or 2.

In a particular embodiment, in the compound of formula (I), when m is 1, Y is in an ortho position and X and Y are each selected independently from the group consisting of methyl, ethyl, iso-propyl and n-propyl.

In another embodiment, preferably combined with the previous embodiment, wherein when n is 1 in the compound of formula (I), Z is in the para position and is selected from the group consisting of fluoro, bromo and chloro, methyl, ethyl, iso-propyl and n-propyl. Preferably, Z is methyl, fluoro, bromo and chloro. More preferably, Z is chloro or methyl.

In another embodiment, wherein in the compound of formula (I), m and n are each 1, Y is in an ortho position and X and Y are selected independently from the group consisting of methyl and ethyl, and Z is in the para position and is selected from the group consisting of fluoro, bromo and chloro. Preferably, X and Y are each in an ortho position and are methyl and preferably Z is in a para position and is chloro or methyl.

In the compounds of the formula (I), the substituent A is preferably hydrogen, $C_{1-4}$alkyl, $C_{1-4}$haloalkyl, $C_{2-4}$alkenyl, $C_{1-4}$alkoxy($C_{1-4}$)alkyl, $C_{1-4}$alkoxy($C_{1-4}$)alkoxy($C_{1-4}$)alkyl, tetrahydrofuranyl, tetrahydropyranyl, in particular methyl, ethyl, n-propyl, iso-propyl, n-butyl, iso-butyl, sec-butyl, and tert-butyl, trifluoromethyl, 2,2,2-trifluoroethyl, 2,2-difluoroethyl, 2-fluoroethyl, allyl, methoxymethyl, ethoxymethyl, methoxyethyl, methoxypropyl, methoxyethoxymethyl, methoxymethoxyethyl, tetrahydrofuran-2-yl, tetrahydropyran-2-yl, tetrahydrofuran-3-yl, tetrahydropyran-4-yl.

In the compounds of the formula (I), Q is preferably (i).

In one embodiment, when Q is (i), A is preferably hydrogen.

In another embodiment, when Q is (i), A is selected from the group consisting of methyl, ethyl, n-propyl, iso-propyl, n-butyl, iso-butyl, sec-butyl, tert-butyl, methoxymethyl, ethoxymethyl and methoxyethyl. Preferably, when Q is (i), A is methyl.

In another embodiment, when Q is (ii), A is selected from the group consisting of hydrogen, methyl, ethyl, n-propyl, iso-propyl, n-butyl, iso-butyl, tert-butyl, methoxymethyl, ethoxymethyl, methoxyethyl, methoxypropyl, tetrahydrofuran-2-yl, tetrahydropyran-2-yl, tetrahydrofuran-3-yl and tetrahydropyran-4-yl. Preferably, when Q is (ii), A is hydrogen, methyl, ethyl, methoxymethyl, and tetrahydrofuran-2-yl.

In another preferred group of compounds of the formula (I), R is one of hydrogen, methyl, ethyl or trifluoromethyl, X is methyl, ethyl or methoxy, Y and Z, independently of each other, are methyl, ethyl, methoxy, fluoro, chloro or bromo, G is hydrogen or —(C═O)—O—$CH_2CH_3$ and A has the meanings assigned to it above.

In a particularly preferred group of compounds of the formula (I), R is methyl or ethyl, X is methyl, ethyl, methoxy, fluoro, bromo or chloro, Y and Z, independently of each other, are methyl, ethyl, methoxy, fluoro, chloro, or bromo, G is hydrogen or —(C═O)—O—$CH_2CH_3$ and A has the meanings assigned to it above.

In a more preferred group of compounds of the formula (I), R is methyl or ethyl, X is methyl, ethyl, methoxy, fluoro, bromo or chloro, Y and Z, independently of each other, are methyl, ethyl, methoxy, fluoro, chloro, bromo, G is hydrogen or —(C═O)—O—$CH_2CH_3$ and A is hydrogen, methyl, ethyl, isopropyl, trifluoromethyl, 2,2,2-trifluoroethyl, 2,2-difluoroethyl, 2-fluoroethyl, tetrahydrofuran-2-ylmethyl, tetrahydropyran-2-ylmethyl, tetrahydrofuran-3-ylmethyl, tetrahydropyran-3-ylmethyl, tetrahydropyran-4-ylmethyl, allyl, methoxymethyl, ethoxymethyl, methoxyethyl, methoxypropyl, methoxyethoxymethyl, methoxymethoxyethyltetrahydrofuran-2-yl, tetrahydropyran-2-yl, tetrahydrofuran-3-yl, or tetrahydropyran-4-yl.

In a another preferred group of compounds of the formula (I), R is methyl, X is methyl or methoxy, Y and Z, independently of each other, are methyl, ethyl, methoxy, chloro or bromo, G is hydrogen, methoxycarbonyl or propenyloxycarbonyl or —(C═O)—O—$CH_2CH_3$, and A is hydrogen, methyl, ethyl, methoxymethyl, tetrahydrofuran-2-yl or tetrahydrofuran-3-yl.

In a another preferred group of compounds of the formula (I), Q is (i), m is 1, n is 1, X is methyl, Y is in the ortho position and is methyl, Z is in the para position and is chloro, G is hydrogen or —(C═O)—O—$CH_2CH_3$, A is methyl, R is methyl.

In a another preferred group of compounds of the formula (I), Q is (i), m is 1, n is 1, X is methyl, Y is in the ortho position and is methyl, Z is in the para position and is chloro, G is hydrogen or —(C═O)—O—$CH_2CH_3$, A is hydrogen, R is methyl.

The compounds of formula (I) according to the following Tables below can be prepared according to the methods disclosed in the art mentioned above.

TABLE 1

This table discloses the 107 compounds T1.001 to T1.107 of the subformula (Ia):

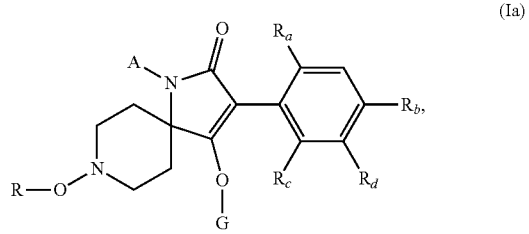

(Ia)

wherein R is $CH_3$, A is $CH_3$, G is —(C═O)—O—$CH_2CH_3$ and $R_a$, $R_b$, $R_c$ and $R_d$ are as defined below:

| No. | $R_a$ | $R_b$ | $R_c$ | $R_d$ |
|---|---|---|---|---|
| T1.001 | Br | H | H | H |
| T1.002 | Cl | H | H | H |
| T1.003 | $CH_3$ | H | H | H |
| T1.004 | $CH_2CH_3$ | H | H | H |
| T1.005 | $OCH_3$ | H | H | H |
| T1.006 | Br | Cl | H | H |
| T1.007 | Cl | Br | H | H |
| T1.008 | Cl | Cl | H | H |
| T1.009 | Cl | $CH_3$ | H | H |
| T1.010 | $CH_3$ | Cl | H | H |
| T1.011 | $CH_3$ | $CH_3$ | H | H |
| T1.012 | Cl | H | Cl | H |
| T1.013 | Cl | H | $CH_3$ | H |
| T1.014 | Cl | H | $CH_2CH_3$ | H |
| T1.015 | Cl | H | $OCH_3$ | H |
| T1.016 | $CH_3$ | H | $CH_3$ | H |
| T1.017 | $CH_3$ | H | $CH_2CH_3$ | H |
| T1.018 | $CH_3$ | H | $OCH_3$ | H |
| T1.019 | $CH_2CH_3$ | H | $CH_2CH_3$ | H |
| T1.020 | $CH_2CH_3$ | H | $OCH_3$ | H |
| T1.021 | $OCH_3$ | H | $OCH_3$ | H |
| T1.022 | Br | H | H | Cl |
| T1.023 | Br | H | H | $CH_3$ |

TABLE 1-continued

This table discloses the 107 compounds T1.001 to T1.107 of the subformula (Ia):

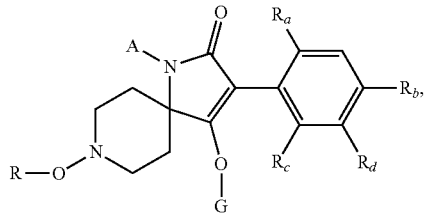

(Ia)

wherein R is $CH_3$, A is $CH_3$, G is —(C=O)—O—$CH_2CH_3$ and $R_a$, $R_b$, $R_c$ and $R_d$ are as defined below:

| No. | $R_a$ | $R_b$ | $R_c$ | $R_d$ |
|---|---|---|---|---|
| T1.024 | Cl | H | H | Cl |
| T1.025 | Cl | H | H | $CH_3$ |
| T1.026 | $CH_3$ | H | H | Br |
| T1.027 | $CH_3$ | H | H | Cl |
| T1.028 | $CH_3$ | H | H | $CH_3$ |
| T1.029 | $CH_2CH_3$ | H | H | $CH_3$ |
| T1.030 | $OCH_3$ | H | H | $CH_3$ |
| T1.031 | Cl | H | Cl | Br |
| T1.032 | $CH_3$ | H | $CH_3$ | Br |
| T1.033 | $CH_3$ | H | $CH_3$ | Cl |
| T1.034 | Br | Cl | H | $CH_3$ |
| T1.035 | Br | $CH_3$ | H | $CH_3$ |
| T1.036 | Cl | Cl | H | Cl |
| T1.037 | Cl | Br | H | $CH_3$ |
| T1.038 | Cl | Cl | H | $CH_3$ |
| T1.039 | Cl | $CH_3$ | H | Cl |
| T1.040 | Cl | $CH_3$ | H | $CH_3$ |
| T1.041 | $CH_3$ | Br | H | $CH_3$ |
| T1.042 | $CH_3$ | Cl | H | $CH_3$ |
| T1.043 | $CH_3$ | $CH_3$ | H | $CH_3$ |
| T1.044 | Br | Br | $CH_3$ | H |
| T1.045 | Br | Cl | $CH_3$ | H |
| T1.046 | Br | $CH_3$ | Br | H |
| T1.047 | Br | $CH_3$ | Cl | H |
| T1.048 | Cl | Br | $CH_3$ | H |
| T1.049 | Cl | Cl | Cl | H |
| T1.050 | Cl | Cl | $CH_3$ | H |
| T1.051 | Cl | $CH_3$ | Cl | H |
| T1.052 | Cl | $CH_3$ | $CH_2CH_3$ | H |
| T1.053 | Cl | $CH_3$ | $OCH_3$ | H |
| T1.054 | $CH_3$ | Br | $CH_3$ | H |
| T1.055 | $CH_3$ | Cl | $CH_3$ | H |
| T1.056 | $CH_3$ | $CH_3$ | Br | H |
| T1.057 | $CH_3$ | $CH_3$ | Cl | H |
| T1.058 | $CH_3$ | $CH_3$ | $CH_3$ | H |
| T1.059 | $CH_3$ | $CH_3$ | $CH_2CH_3$ | H |
| T1.060 | $CH_3$ | $CH_3$ | $OCH_3$ | H |
| T1.061 | $CH_2CH_3$ | Br | Br | H |
| T1.062 | $CH_2CH_3$ | Br | Cl | H |
| T1.063 | $CH_2CH_3$ | Br | $CH_3$ | H |
| T1.064 | $CH_2CH_3$ | Br | $CH_2CH_3$ | H |
| T1.065 | $CH_2CH_3$ | Br | $OCH_3$ | H |
| T1.066 | $CH_2CH_3$ | Cl | Br | H |
| T1.067 | $CH_2CH_3$ | Cl | Cl | H |
| T1.068 | $CH_2CH_3$ | Cl | $CH_3$ | H |
| T1.069 | $CH_2CH_3$ | Cl | $CH_2CH_3$ | H |
| T1.070 | $CH_2CH_3$ | Cl | $OCH_3$ | H |
| T1.071 | $CH_2CH_3$ | $CH_3$ | Br | H |
| T1.072 | $CH_2CH_3$ | $CH_3$ | Cl | H |
| T1.073 | $CH_2CH_3$ | $CH_3$ | $CH_2CH_3$ | H |
| T1.074 | $CH_2CH_3$ | $CH_3$ | $OCH_3$ | H |
| T1.075 | $CH_2CH_3$ | $CH_2CH_3$ | $CH_3$ | H |
| T1.076 | $CH_2CH_3$ | $CH_2CH_3$ | $CH_2CH_3$ | H |
| T1.077 | $OCH_3$ | Br | $CH_3$ | H |
| T1.078 | $OCH_3$ | Cl | $CH_3$ | H |
| T1.079 | $OCH_3$ | $CH_3$ | Br | H |
| T1.080 | $OCH_3$ | $CH_3$ | Cl | H |
| T1.081 | $OCH_3$ | $CH_3$ | $OCH_3$ | H |
| T1.082 | $CH_3$ | $CH_3$ | $CH_3$ | F |
| T1.083 | $CH_3$ | $CH_3$ | $CH_3$ | Cl |
| T1.084 | $CH_3$ | $CH_3$ | $CH_3$ | Br |
| T1.085 | $CH_3$ | $CH_3$ | $CH_3$ | $CH_3$ |
| T1.086 | Cl | $CH_3$ | $CH_3$ | $CH_3$ |
| T1.087 | $CH_3$ | Cl | $CH_3$ | $CH_3$ |
| T1.088 | $CH_3$ | $CH_3$ | Cl | $CH_3$ |
| T1.089 | $CH_2CH_3$ | $CH_3$ | $CH_3$ | $CH_3$ |
| T1.090 | $OCH_3$ | $CH_3$ | $CH_3$ | $CH_3$ |
| T1.091 | $CH_3$ | F | H | Br |
| T1.092 | $CH_3$ | $CH_3$ | H | Br |
| T1.093 | $CH_2CH_3$ | $CH_3$ | H | $CH_3$ |
| T1.094 | $OCH_3$ | $CH_3$ | H | $CH_3$ |
| T1.095 | $CH_2CH_3$ | Cl | H | $CH_3$ |
| T1.096 | $OCH_3$ | Cl | H | $CH_3$ |
| T1.097 | Cl | H | $CH_3$ | $CH_3$ |
| T1.098 | $CH_3$ | H | $CH_3$ | $CH_3$ |
| T1.099 | $CH_2CH_3$ | H | $CH_3$ | $CH_3$ |
| T1.100 | $OCH_3$ | H | $CH_3$ | $CH_3$ |
| T1.101 | F | H | Cl | $CH_3$ |
| T1.102 | Cl | H | F | $CH_3$ |
| T1.103 | H | $CH_3$ | $CH_3$ | $CH_3$ |
| T1.104 | Br | $CH_3$ | $CH_3$ | $CH_3$ |
| T1.105 | $CH_3$ | H | Cl | $CH_3$ |
| T1.106 | $CH_3$ | H | Br | $CH_3$ |
| T1.107 | Br | H | $CH_3$ | $CH_3$ |

Table 2: This table discloses the 107 compounds T2.001 to T2.107 of the formula (Ia), wherein R is $CH_3$, A is $CH_2CH_3$, G is —(C=O)—O—$CH_2CH_3$ and $R_a$, $R_b$, $R_c$ and $R_d$ are as defined in Table 1.

Table 3: This table discloses the 107 compounds T3.001 to T3.107 of the formula (Ia), wherein R is $CH_3$, A is n-$C_3H_7$, G is —(C=O)—O—$CH_2CH_3$ and $R_a$, $R_b$, $R_c$ and $R_d$ are as defined in Table 1.

Table 4: This table discloses the 107 compounds T4.001 to T4.107 of the formula (Ia), wherein R is $CH_3$, A is i-$C_3H_7$, G is —(C=O)—O—$CH_2CH_3$ and $R_a$, $R_b$, $R_c$ and $R_d$ are as defined in Table 1.

Table 5: This table discloses the 107 compounds T5.001 to T5.107 of the formula (Ia), wherein R is $CH_3$, A is n-$C_4H_9$, G is —(C=O)—O—$CH_2CH_3$ and $R_a$, $R_b$, $R_c$ and $R_d$ are as defined in Table 1.

Table 6: This table discloses the 107 compounds T6.001 to T6.107 of the formula (Ia), wherein R is $CH_3$, A is i-$C_4H_9$, G is hydrogen and $R_a$, $R_b$, $R_c$ and $R_d$ are as defined in Table 1.

Table 7: This table discloses the 107 compounds T7.001 to T7.107 of the formula (Ia), wherein R is $CH_3$, A is t-$C_4H_9$, G is —(C=O)—O—$CH_2CH_3$ and $R_a$, $R_b$, $R_c$ and $R_d$ are as defined in Table 1.

Table 8: This table discloses the 107 compounds T8.001 to T8.107 of the formula (Ia), wherein R is $CH_3$, A is 2,2-$(CH_3)_2$-propyl, G is —(C=O)—O—$CH_2CH_3$ and $R_a$, $R_b$, $R_c$ and $R_d$ are as defined in Table 1.

Table 9: This table discloses the 107 compounds T9.001 to T9.107 of the formula (Ia), wherein R is $CH_3$, A is allyl, G is —(C=O)—O—$CH_2CH_3$ and $R_a$, $R_b$, $R_c$ and $R_d$ are as defined in Table 1.

Table 10: This table discloses the 107 compounds T10.001 to T10.107 of the formula (Ia), wherein R is $CH_3$, A is $CH_2$—CH=$C(CH_3)_2$, G is —(C=O)—O—$CH_2CH_3$ and $R_a$, $R_b$, $R_c$ and $R_d$ are as defined in Table 1.

Table 11: This table discloses the 107 compounds T11.001 to T11.107 of the formula (Ia), wherein R is $CH_3$, A is $CH_2$—CH=$C(Cl)_2$, G is —(C=O)—O—$CH_2CH_3$ and $R_a$, $R_b$, $R_c$ and $R_d$ are as defined in Table 1.

Table 12: This table discloses the 107 compounds T12.001 to T12.107 of the formula (Ia), wherein R is $CH_3$, A is $CH_2OCH_3$, G is —(C=O)—O—$CH_2CH_3$ and $R_a$, $R_b$, $R_c$ and $R_d$ are as defined in Table 1.

Table 13: This table discloses the 107 compounds T13.001 to T13.107 of the formula (Ia), wherein R is $CH_3$, A is $CH_2OCH_2CH_3$, G is —(C=O)—O—$CH_2CH_3$ and $R_a$, $R_b$, $R_c$ and $R_d$ are as defined in Table 1.

Table 14: This table discloses the 107 compounds T14.001 to T14.107 of the formula (Ia), wherein R is $CH_3$, A is $CH_2CH_2OCH_3$, G is —(C=O)—O—$CH_2CH_3$ and $R_a$, $R_b$, $R_c$ and $R_d$ are as defined in Table 1.

Table 15: This table discloses the 107 compounds T15.001 to T15.107 of the formula (Ia), wherein R is $CH_3$, A is $CH_2OCH_2CH_2OCH_3$, G is —(C=O)—O—$CH_2CH_3$ and $R_a$, $R_b$, $R_c$ and $R_d$ are as defined in Table 1.

Table 16: This table discloses the 107 compounds T16.001 to T16.107 of the formula (Ia), wherein R is $CH_3$, A is $CH_2CH_2OCH_2OCH_3$, G is —(C=O)—O—$CH_2CH_3$ and $R_a$, $R_b$, $R_c$ and $R_d$ are as defined in Table 1.

Table 17: This table discloses the 107 compounds T17.001 to T17.107 of the formula (Ia), wherein R is $CH_3$, A is tetrahydrofuran-2-yl, G is —(C=O)—O—$CH_2CH_3$ and $R_a$, $R_b$, $R_c$ and $R_d$ are as defined in Table 1.

Table 18: This table discloses the 107 compounds T18.001 to T18.107 of the formula (Ia), wherein R is $CH_3$, A is tetrahydrofuran-3-yl, G is —(C=O)—O—$CH_2CH_3$ and $R_a$, $R_b$, $R_c$ and $R_d$ are as defined in Table 1.

Table 19: This table discloses the 107 compounds T19.001 to T19.107 of the formula (Ia), wherein R is $CH_3$, A is tetrahydropyran-2-yl, G is —(C=O)—O—$CH_2CH_3$ and $R_a$, $R_b$, $R_c$ and $R_d$ are as defined in Table 1.

Table 20: This table discloses the 107 compounds T20.001 to T20.107 of the formula (Ia), wherein R is $CH_3$, A is tetrahydropyran-4-yl, G is —(C=O)—O—$CH_2CH_3$ and $R_a$, $R_b$, $R_c$ and $R_d$ are as defined in Table 1.

Table 21: This table discloses the 107 compounds T21.001 to T21.107 of the formula (Ia), wherein R is $CH_3$, A is $CH_2CH_2F$, G is —(C=O)—O—$CH_2CH_3$ and $R_a$, $R_b$, $R_c$ and $R_d$ are as defined in Table 1.

Table 22: This table discloses the 107 compounds T22.001 to T22.107 of the formula (Ia), wherein R is $CH_3$, A is $CH_2CHF_2$, G is —(C=O)—O—$CH_2CH_3$ and $R_a$, $R_b$, $R_c$ and $R_d$ are as defined in Table 1.

Table 23: This table discloses the 107 compounds T23.001 to T23.107 of the formula (Ia), wherein R is $CH_3$, A is $CH_2CF_3$, G is hydrogen and $R_a$, $R_b$, $R_c$ and $R_d$ are as defined in Table 1.

Table 24: This table discloses the 107 compounds T24.001 to T24.107 of the formula (Ia), wherein R is hydrogen, A is $CH_3$, G is —(C=O)—O—CH2CH3 and $R_a$, $R_b$, $R_c$ and $R_d$ are as defined in Table 1.

Table 25: This table discloses the 107 compounds T25.001 to T25.107 of the formula (Ia), wherein R is hydrogen, A is $CH_2CH_3$, G is —(C=O)—O—CH2CH3 and $R_a$, $R_b$, $R_c$ and $R_d$ are as defined in Table 1.

Table 26: This table discloses the 107 compounds T26.001 to T26.107 of the formula (Ia), wherein R is hydrogen, A is i-$C_3H_7$, G is —(C=O)—O—CH2CH3 and $R_a$, $R_b$, $R_c$ and $R_d$ are as defined in Table 1.

Table 27: This table discloses the 107 compounds T27.001 to T27.107 of the formula (Ia), wherein R is hydrogen, A is $CH_2OCH_3$, G is —(C=O)—O—CH2CH3 and $R_a$, $R_b$, $R_c$ and $R_d$ are as defined in Table 1.

Table 28: This table discloses the 107 compounds T28.001 to T28.107 of the formula (Ia), wherein R is hydrogen, A is $CH_2CH_2OCH_3$, G is —(C=O)—O—CH2CH3 and $R_a$, $R_b$, $R_c$ and $R_d$ are as defined in Table 1.

Table 29: This table discloses the 107 compounds T29.001 to T29.107 of the formula (Ia), wherein R is hydrogen, A is $CH_2OCH_2CH_2OCH_3$, G is —(C=O)—O—CH2CH3 and $R_a$, $R_b$, $R_c$ and $R_d$ are as defined in Table 1.

Table 30: This table discloses the 107 compounds T30.001 to T30.107 of the formula (Ia), wherein R is hydrogen, A is $CH_2CH_2OCH_2OCH_3$, G is —(C=O)—O—CH2CH3 and $R_a$, $R_b$, $R_c$ and $R_d$ are as defined in Table 1.

Table 31: This table discloses the 107 compounds T31.001 to T31.107 of the formula (Ia), wherein R is hydrogen, A is $CH_2CHF_2$, G is —(C=O)—O—CH2CH3 and $R_a$, $R_b$, $R_c$ and $R_d$ are as defined in Table 1.

Table 32: This table discloses the 107 compounds T32.001 to T32.107 of the formula (Ia), wherein R is hydrogen, A is $CH_2CF_3$, G is —(C=O)—O—CH2CH3 and $R_a$, $R_b$, $R_c$ and $R_d$ are as defined in Table 1.

Table 33: This table discloses the 107 compounds T33.001 to T33.107 of the formula (Ia), wherein R is $CH_2CH_3$, A is $CH_3$, G is —(C=O)—O—CH2CH3 and $R_a$, $R_b$, $R_c$ and $R_d$ are as defined in Table 1.

Table 34: This table discloses the 107 compounds T34.001 to T34.107 of the formula (Ia), wherein R is $CH_2CH_3$, A is $CH_2CH_3$, G is —(C=O)—O—CH2CH3 and $R_a$, $R_b$, $R_c$ and $R_d$ are as defined in Table 1.

Table 35: This table discloses the 107 compounds T35.001 to T35.107 of the formula (Ia), wherein R is $CH_2CH_3$, A is i-$C_3H_7$, G is —(C=O)—O—CH2CH3 and $R_a$, $R_b$, $R_c$ and $R_d$ are as defined in Table 1.

Table 36: This table discloses the 107 compounds T36.001 to T36.107 of the formula (Ia), wherein R is $CH_2CH_3$, A is $CH_2OCH_3$, G is —(C=O)—O—CH2CH3 and $R_a$, $R_b$, $R_c$ and $R_d$ are as defined in Table 1.

Table 37: This table discloses the 107 compounds T37.001 to T37.107 of the formula (Ia), wherein R is $CH_2CH_3$, A is $CH_2CH_2OCH_3$, G is —(C=O)—O—CH2CH3 and $R_a$, $R_b$, $R_c$ and $R_d$ are as defined in Table 1.

Table 38: This table discloses the 107 compounds T38.001 to T38.107 of the formula (Ia), wherein R is $CH_2CH_3$, A is $CH_2OCH_2CH_2OCH_3$, G is —(C=O)—O—CH2CH3 and $R_a$, $R_b$, $R_c$ and $R_d$ are as defined in Table 1.

Table 39: This table discloses the 107 compounds T39.001 to T39.107 of the formula (Ia), wherein R is $CH_2CH_3$, A is $CH_2CH_2OCH_2OCH_3$, G is —(C=O)—O—CH2CH3 and $R_a$, $R_b$, $R_c$ and $R_d$ are as defined in Table 1.

Table 40: This table discloses the 107 compounds T40.001 to T40.107 of the formula (Ia), wherein R is $CH_2CH_3$, A is $CH_2CHF_2$, G is —(C=O)—O—CH2CH3 and $R_a$, $R_b$, $R_c$ and $R_d$ are as defined in Table 1.

Table 41: This table discloses the 107 compounds T41.001 to T41.107 of the formula (Ia), wherein R is $CH_2CH_3$, A is $CH_2CF_3$, G is —(C=O)—O—CH2CH3 and $R_a$, $R_b$, $R_c$ and $R_d$ are as defined in Table 1.

Table 42: This table discloses the 107 compounds T42.001 to T42.107 of the formula (Ia), wherein R is CH₃, A is methoxypropyl, G is —(C=O)—O—CH2CH3 and $R_a$, $R_b$, $R_c$ and $R_d$ are as defined in Table 1.

Table 43: This table discloses the 107 compounds T43.001 to T43.107 of the formula (Ia), wherein R is H, A is methoxypropyl, G is —(C=O)—O—CH2CH3 and $R_a$, $R_b$, $R_c$ and $R_d$ are as defined in Table 1.

Table 44: This table discloses the 107 compounds T44.001 to T44.107 of the formula (Ia), wherein R is CH₂CH₃, A is methoxypropyl, G is —(C=O)—O—CH2CH3 and $R_a$, $R_b$, $R_c$ and $R_d$ are as defined in Table 1.

TABLE 1ii

This table discloses the 107 compounds T1ii.001 to T1ii.107 of the subformula (Ib):

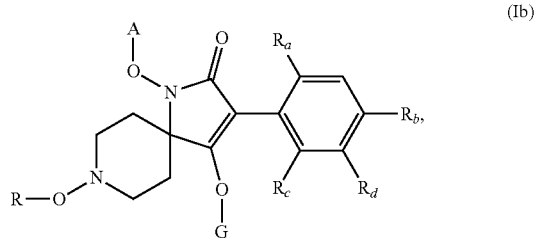

(Ib)

wherein R is CH₃, A is hydrogen, G is —(C=O)—O—CH2CH3 and $R_a$, $R_b$, $R_c$ and $R_d$ are as defined below:

| No. | $R_a$ | $R_b$ | $R_c$ | $R_d$ |
|---|---|---|---|---|
| T1ii.001 | Br | H | H | H |
| T1ii.002 | Cl | H | H | H |
| T1ii.003 | CH₃ | H | H | H |
| T1ii.004 | CH₂CH₃ | H | H | H |
| T1ii.005 | OCH₃ | H | H | H |
| T1ii.006 | Br | Cl | H | H |
| T1ii.007 | Cl | Br | H | H |
| T1ii.008 | Cl | Cl | H | H |
| T1ii.009 | Cl | CH₃ | H | H |
| T1ii.010 | CH₃ | Cl | H | H |
| T1ii.011 | CH₃ | CH₃ | H | H |
| T1ii.012 | Cl | H | Cl | H |
| T1ii.013 | Cl | H | CH₃ | H |
| T1ii.014 | Cl | H | CH₂CH₃ | H |
| T1ii.015 | Cl | H | OCH₃ | H |
| T1ii.016 | CH₃ | H | CH₃ | H |
| T1ii.017 | CH₃ | H | CH₂CH₃ | H |
| T1ii.018 | CH₃ | H | OCH₃ | H |
| T1ii.019 | CH₂CH₃ | H | CH₂CH₃ | H |
| T1ii.020 | CH₂CH₃ | H | OCH₃ | H |
| T1ii.021 | OCH₃ | H | OCH₃ | H |
| T1ii.022 | Br | H | H | Cl |
| T1ii.023 | Br | H | H | CH₃ |
| T1ii.024 | Cl | H | H | Cl |
| T1ii.025 | Cl | H | H | CH₃ |
| T1ii.026 | CH₃ | H | H | Br |
| T1ii.027 | CH₃ | H | H | Cl |
| T1ii.028 | CH₃ | H | H | CH₃ |
| T1ii.029 | CH₂CH₃ | H | H | CH₃ |
| T1ii.030 | OCH₃ | H | H | CH₃ |
| T1ii.031 | Cl | H | Cl | Br |
| T1ii.032 | CH₃ | H | CH₃ | Br |
| T1ii.033 | CH₃ | H | CH₃ | Cl |
| T1ii.034 | Br | Cl | H | CH₃ |
| T1ii.035 | Br | CH₃ | H | CH₃ |
| T1ii.036 | Cl | Cl | H | Cl |
| T1ii.037 | Cl | Br | H | CH₃ |
| T1ii.038 | Cl | Cl | H | CH₃ |
| T1ii.039 | Cl | CH₃ | H | Cl |
| T1ii.040 | Cl | CH₃ | H | CH₃ |
| T1ii.041 | CH₃ | Br | H | CH₃ |
| T1ii.042 | CH₃ | Cl | H | CH₃ |
| T1ii.043 | CH₃ | CH₃ | H | CH₃ |

TABLE 1ii-continued

This table discloses the 107 compounds T1ii.001 to T1ii.107 of the subformula (Ib):

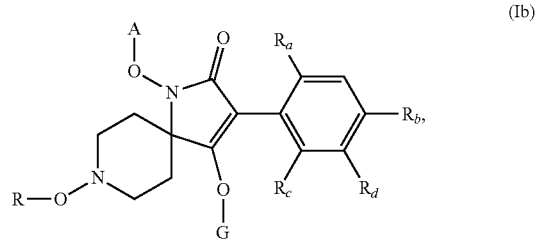

(Ib)

wherein R is CH₃, A is hydrogen, G is —(C=O)—O—CH2CH3 and $R_a$, $R_b$, $R_c$ and $R_d$ are as defined below:

| No. | $R_a$ | $R_b$ | $R_c$ | $R_d$ |
|---|---|---|---|---|
| T1ii.044 | Br | Br | CH₃ | H |
| T1ii.045 | Br | Cl | CH₃ | H |
| T1ii.046 | Br | CH₃ | Br | H |
| T1ii.047 | Br | CH₃ | Cl | H |
| T1ii.048 | Cl | Br | CH₃ | H |
| T1ii.049 | Cl | Cl | Cl | H |
| T1ii.050 | Cl | Cl | CH₃ | H |
| T1ii.051 | Cl | CH₃ | Cl | H |
| T1ii.052 | Cl | CH₃ | CH₂CH₃ | H |
| T1ii.053 | Cl | CH₃ | OCH₃ | H |
| T1ii.054 | CH₃ | Br | CH₃ | H |
| T1ii.055 | CH₃ | Cl | CH₃ | H |
| T1ii.056 | CH₃ | CH₃ | Br | H |
| T1ii.057 | CH₃ | CH₃ | Cl | H |
| T1ii.058 | CH₃ | CH₃ | CH₃ | H |
| T1ii.059 | CH₃ | CH₃ | CH₂CH₃ | H |
| T1ii.060 | CH₃ | CH₃ | OCH₃ | H |
| T1ii.061 | CH₂CH₃ | Br | Br | H |
| T1ii.062 | CH₂CH₃ | Br | Cl | H |
| T1ii.063 | CH₂CH₃ | Br | CH₃ | H |
| T1ii.064 | CH₂CH₃ | Br | CH₂CH₃ | H |
| T1ii.065 | CH₂CH₃ | Br | OCH₃ | H |
| T1ii.066 | CH₂CH₃ | Cl | Br | H |
| T1ii.067 | CH₂CH₃ | Cl | Cl | H |
| T1ii.068 | CH₂CH₃ | Cl | CH₃ | H |
| T1ii.069 | CH₂CH₃ | Cl | CH₂CH₃ | H |
| T1ii.070 | CH₂CH₃ | Cl | OCH₃ | H |
| T1ii.071 | CH₂CH₃ | CH₃ | Br | H |
| T1ii.072 | CH₂CH₃ | CH₃ | Cl | H |
| T1ii.073 | CH₂CH₃ | CH₃ | CH₂CH₃ | H |
| T1ii.074 | CH₂CH₃ | CH₃ | OCH₃ | H |
| T1ii.075 | CH₂CH₃ | CH₂CH₃ | CH₃ | H |
| T1ii.076 | CH₂CH₃ | CH₂CH₃ | CH₂CH₃ | H |
| T1ii.077 | OCH₃ | Br | CH₃ | H |
| T1ii.078 | OCH₃ | Cl | CH₃ | H |
| T1ii.079 | OCH₃ | CH₃ | Br | H |
| T1ii.080 | OCH₃ | CH₃ | Cl | H |
| T1ii.081 | OCH₃ | CH₃ | OCH₃ | H |
| T1ii.082 | CH₃ | CH₃ | CH₃ | F |
| T1ii.083 | CH₃ | CH₃ | CH₃ | Cl |
| T1ii.084 | CH₃ | CH₃ | CH₃ | Br |
| T1ii.085 | CH₃ | CH₃ | CH₃ | CH₃ |
| T1ii.086 | Cl | CH₃ | CH₃ | CH₃ |
| T1ii.087 | CH₃ | Cl | CH₃ | CH₃ |
| T1ii.088 | CH₃ | CH₃ | Cl | CH₃ |
| T1ii.089 | CH₂CH₃ | CH₃ | CH₃ | CH₃ |
| T1ii.090 | OCH₃ | CH₃ | CH₃ | CH₃ |
| T1ii.091 | CH₃ | F | H | Br |
| T1ii.092 | CH₃ | CH₃ | H | Br |
| T1ii.093 | CH₂CH₃ | CH₃ | H | CH₃ |
| T1ii.094 | OCH₃ | CH₃ | H | CH₃ |
| T1ii.095 | CH₂CH₃ | Cl | H | CH₃ |
| T1ii.096 | OCH₃ | Cl | H | CH₃ |
| T1ii.097 | Cl | H | CH₃ | CH₃ |
| T1ii.098 | CH₃ | H | CH₃ | CH₃ |
| T1ii.099 | CH₂CH₃ | H | CH₃ | CH₃ |
| T1ii.100 | OCH₃ | H | CH₃ | CH₃ |
| T1ii.101 | F | H | Cl | CH₃ |
| T1ii.102 | Cl | H | F | CH₃ |

TABLE 1ii-continued

This table discloses the 107 compounds T1ii.001 to T1ii.107 of the subformula (Ib):

(Ib)

wherein R is CH$_3$, A is hydrogen, G is —(C=O)—O—CH2CH3 and R$_a$, R$_b$, R$_c$ and R$_d$ are as defined below:

| No. | R$_a$ | R$_b$ | R$_c$ | R$_d$ |
|---|---|---|---|---|
| T1ii.103 | H | CH$_3$ | CH$_3$ | CH$_3$ |
| T1ii.104 | Br | CH$_3$ | CH$_3$ | CH$_3$ |
| T1ii.105 | CH$_3$ | H | Cl | CH$_3$ |
| T1ii.106 | CH$_3$ | H | Br | CH$_3$ |
| T1ii.107 | Br | H | CH$_3$ | CH$_3$ |

Table 2ii: This table discloses the 107 compounds T2ii.001 to T2ii.107 of the formula (Ib), wherein R is CH$_3$, A is CH$_3$, G is —(C=O)—O—CH2CH3 and R$_a$, R$_b$, R$_c$ and R$_d$ are as defined in Table 1ii.

Table 3ii: This table discloses the 107 compounds T3ii.001 to T3ii.107 of the formula (Ib), wherein R is CH$_3$, A is CH$_2$CH$_3$, G is —(C=O)—O—CH2CH3 and R$_a$, R$_b$, R$_c$ and R$_d$ are as defined in Table 1ii.

Table 4ii: This table discloses the 107 compounds T4ii.001 to T4ii.107 of the formula (Ib), wherein R is CH$_3$, A is n-C$_3$H$_7$, G is —(C=O)—O—CH2CH3 and R$_a$, R$_b$, R$_c$ and R$_d$ are as defined in Table 1ii.

Table 5ii: This table discloses the 107 compounds T5ii.001 to T5ii.107 of the formula (Ib), wherein R is CH$_3$, A is i-C$_3$H$_7$, G is —(C=O)—O—CH2CH3 and R$_a$, R$_b$, R$_c$ and R$_d$ are as defined in Table 1ii.

Table 6ii: This table discloses the 107 compounds T6ii.001 to T6ii.107 of the formula (Ib), wherein R is CH$_3$, A is n-C$_4$H$_9$, G is —(C=O)—O—CH2CH3 and R$_a$, R$_b$, R$_c$ and R$_d$ are as defined in Table 1ii.

Table 7ii: This table discloses the 107 compounds T7ii.001 to T7ii.107 of the formula (Ib), wherein R is CH$_3$, A is i-C$_4$H$_9$, G is —(C=O)—O—CH2CH3 and R$_a$, R$_b$, R$_c$ and R$_d$ are as defined in Table 1ii.

Table 8ii: This table discloses the 107 compounds T8ii.001 to T8ii.107 of the formula (Ib), wherein R is CH$_3$, A is t-C$_4$H$_9$, G is —(C=O)—O—CH2CH3 and R$_a$, R$_b$, R$_c$ and R$_d$ are as defined in Table 1ii.

Table 9ii: This table discloses the 107 compounds T9ii.001 to T9ii.107 of the formula (Ib), wherein R is CH$_3$, A is 2,2-(CH$_3$)$_2$-propyl, G is —(C=O)—O—CH2CH3 and R$_a$, R$_b$, R$_c$ and R$_d$ are as defined in Table 1ii.

Table 10ii: This table discloses the 107 compounds T10ii.001 to T10ii.107 of the formula (Ib), wherein R is CH$_3$, A is allyl, G is —(C=O)—O—CH2CH3 and R$_a$, R$_b$, R$_c$ and R$_d$ are as defined in Table 1ii.

Table 11ii: This table discloses the 107 compounds T11ii.001 to T11ii.107 of the formula (Ib), wherein R is CH$_3$, A is CH$_2$—CH=C(CH$_3$)$_2$, G is —(C=O)—O—CH2CH3 and R$_a$, R$_b$, R$_c$ and R$_d$ are as defined in Table 1ii.

Table 12ii: This table discloses the 107 compounds T12ii.001 to T12ii.107 of the formula (Ib), wherein R is CH$_3$, A is CH$_2$—CH=C(Cl)$_2$, G is —(C=O)—O—CH2CH3 and R$_a$, R$_b$, R$_c$ and R$_d$ are as defined in Table 1ii.

Table 13ii: This table discloses the 107 compounds T13ii.001 to T13ii.107 of the formula (Ib), wherein R is CH$_3$, A is CH$_2$OCH$_3$, G is —(C=O)—O—CH2CH3 and R$_a$, R$_b$, R$_c$ and R$_d$ are as defined in Table 1ii.

Table 14ii: This table discloses the 107 compounds T14ii.001 to T14ii.107 of the formula (Ib), wherein R is CH$_3$, A is CH$_2$OCH$_2$CH$_3$, G is —(C=O)—O—CH2CH3 and R$_a$, R$_b$, R$_c$ and R$_d$ are as defined in Table 1ii.

Table 15ii: This table discloses the 107 compounds T15ii.001 to T15ii.107 of the formula (Ib), wherein R is CH$_3$, A is CH$_2$CH$_2$OCH$_3$, G is —(C=O)—O—CH2CH3 and R$_a$, R$_b$, R$_c$ and R$_d$ are as defined in Table 1ii.

Table 16ii: This table discloses the 107 compounds T16ii.001 to T16ii.107 of the formula (Ib), wherein R is CH$_3$, A is CH$_2$OCH$_2$CH$_2$OCH$_3$, G is —(C=O)—O—CH2CH3 and R$_a$, R$_b$, R$_c$ and R$_d$ are as defined in Table 1ii.

Table 17ii: This table discloses the 107 compounds T17ii.001 to T17ii.107 of the formula (Ib), wherein R is CH$_3$, A is tetrahydrofuran-2-yl, G is —(C=O)—O—CH2CH3 and R$_a$, R$_b$, R$_c$ and R$_d$ are as defined in Table 1ii.

Table 18ii: This table discloses the 107 compounds T18ii.001 to T18ii.107 of the formula (Ib), wherein R is CH$_3$, A is tetrahydrofuran-3-yl, G is hydrogen and R$_a$, R$_b$, R$_c$ and R$_d$ are as defined in Table 1ii.

Table 19ii: This table discloses the 107 compounds T19ii.001 to T19ii.107 of the formula (Ib), wherein R is CH$_3$, A is tetrahydropyran-2-yl, G is —(C=O)—O—CH2CH3 and R$_a$, R$_b$, R$_c$ and R$_d$ are as defined in Table 1ii.

Table 20ii: This table discloses the 107 compounds T20ii.001 to T20ii.107 of the formula (Ib), wherein R is CH$_3$, A is tetrahydropyran-4-yl, G is —(C=O)—O—CH2CH3 and R$_a$, R$_b$, R$_c$ and R$_d$ are as defined in Table 1ii.

Table 21ii: This table discloses the 107 compounds T21ii.001 to T21ii.107 of the formula (Ib), wherein R is CH$_3$, A is CH$_2$CHF$_2$, G is —(C=O)—O—CH2CH3 and R$_a$, R$_b$, R$_c$ and R$_d$ are as defined in Table 1ii.

Table 22ii: This table discloses the 107 compounds T22ii.001 to T22ii.107 of the formula (Ib), wherein R is hydrogen, A is hydrogen, G is —(C=O)—O—CH2CH3 and R$_a$, R$_b$, R$_c$ and R$_d$ are as defined in Table 1ii.

Table 23ii: This table discloses the 107 compounds T23ii.001 to T23ii.107 of the formula (Ib), wherein R is hydrogen, A is CH$_3$, G is —(C=O)—O—CH2CH3 and R$_a$, R$_b$, R$_c$ and R$_d$ are as defined in Table 1ii.

Table 24ii: This table discloses the 107 compounds T24ii.001 to T24ii.107 of the formula (Ib), wherein R is hydrogen, A is CH$_2$OCH$_3$, G is —(C=O)—O—CH2CH3 and R$_a$, R$_b$, R$_c$ and R$_d$ are as defined in Table 1ii.

Table 25ii: This table discloses the 107 compounds T25ii.001 to T25ii.107 of the formula (Ib), wherein R is hydrogen, A is CH$_2$CH$_2$OCH$_3$, G is —(C=O)—O—CH2CH3 and R$_a$, R$_b$, R$_c$ and R$_d$ are as defined in Table 1ii.

Table 26ii: This table discloses the 107 compounds T26ii.001 to T26ii.107 of the formula (Ib), wherein R is CH$_2$CH$_3$, A is hydrogen, G is —(C=O)—O—CH2CH3 and R$_a$, R$_b$, R$_c$ and R$_d$ are as defined in Table 1ii.

Table 27ii: This table discloses the 107 compounds T27ii.001 to T27ii.107 of the formula (Ib), wherein R is CH$_2$CH$_3$, A is CH$_3$, G is —(C=O)—O—CH2CH3 and R$_a$, R$_b$, R$_c$ and R$_d$ are as defined in Table 1ii.

Table 28ii: This table discloses the 107 compounds T28ii.001 to T28ii.107 of the formula (Ib), wherein R is CH$_2$CH$_3$, A is CH$_2$OCH$_3$, G is —(C=O)—O—CH2CH3 and R$_a$, R$_b$, R$_c$ and R$_d$ are as defined in Table 1ii.

Table 29ii: This table discloses the 107 compounds T29ii.001 to T29ii.107 of the formula (Ib), wherein R is CH$_2$CH$_3$, A is CH$_2$CH$_2$OCH$_3$, G is —(C=O)—O—CH2CH3 and R$_a$, R$_b$, R$_c$ and R$_d$ are as defined in Table 1ii.

Table 30ii: This table discloses the 107 compounds T30ii.001 to T30ii.107 of the formula (Ib), wherein R is CH$_3$, A is CH$_2$CH$_2$CH$_2$OCH$_3$, G is —(C=O)—O—CH2CH3 and R$_a$, R$_b$, R$_c$ and R$_d$ are as defined in Table 1ii.

Table 31ii: This table discloses the 107 compounds T31ii.001 to T31ii.107 of the formula (Ib), wherein R is hydrogen, A is CH$_2$CH$_3$, G is —(C=O)—O—CH2CH3 and R$_a$, R$_b$, R$_c$ and R$_d$ are as defined in Table 1ii.

Table 32ii: This table discloses the 107 compounds T32ii.001 to T32ii.107 of the formula (Ib), wherein R is hydrogen, A is allyl, G is —(C=O)—O—CH2CH3 and R$_a$, R$_b$, R$_c$ and R$_d$ are as defined in Table 1ii.

Table 33ii: This table discloses the 107 compounds T33ii.001 to T33ii.107 of the formula (Ib), wherein R is hydrogen, A is tetrahydrofuran-2-yl, G is —(C=O)—O—CH2CH3 and R$_a$, R$_b$, R$_c$ and R$_d$ are as defined in Table 1ii.

Table 34ii: This table discloses the 107 compounds T34ii.001 to T34ii.107 of the formula (Ib), wherein R is hydrogen, A is tetrahydropyran-2-yl, G is —(C=O)—O—CH2CH3 and R$_a$, R$_b$, R$_c$ and R$_d$ are as defined in Table 1ii.

Table 35ii: This table discloses the 107 compounds T35ii.001 to T35ii.107 of the formula (Ib), wherein R is CH$_2$CH$_3$, A is CH$_2$CH$_3$, G is —(C=O)—O—CH2CH3 and R$_a$, R$_b$, R$_c$ and R$_d$ are as defined in Table 1ii.

Table 36ii: This table discloses the 107 compounds T36ii.001 to T36ii.107 of the formula (Ib), wherein R is CH$_2$CH$_3$, A is allyl, G is —(C=O)—O—CH2CH3 and R$_a$, R$_b$, R$_c$ and R$_d$ are as defined in Table 1ii.

Table 37ii: This table discloses the 107 compounds T37ii.001 to T37ii.107 of the formula (Ib), wherein R is CH$_2$CH$_3$, A is tetrahydrofuran-2-yl, G is —(C=O)—O—CH2CH3 and R$_a$, R$_b$, R$_c$ and R$_d$ are as defined in Table 1ii.

Table 38ii: This table discloses the 107 compounds T38ii.001 to T38ii.107 of the formula (Ib), wherein R is CH$_2$CH$_3$, A is tetrahydropyran-2-yl, G is —(C=O)—O—CH2CH3 and R$_a$, R$_b$, R$_c$ and R$_d$ are as defined in Table 1ii.

TABLE 1iii

This table discloses the 87 compounds T1iii.001 to T1iii.87 of the subformula (Ic):

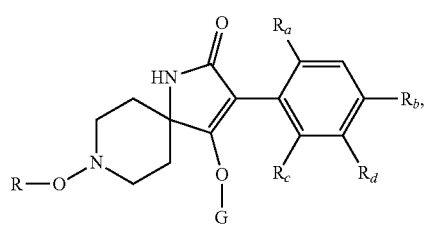

(Ic)

wherein R is CH$_3$, G is —(C=O)—O—CH2CH3 and R$_a$, R$_b$, R$_c$ and R$_d$ are as defined below:

| No. | R$_a$ | R$_b$ | R$_c$ | R$_d$ |
|---|---|---|---|---|
| T1iii.001 | Br | H | H | H |
| T1iii.002 | Cl | H | H | H |
| T1iii.003 | CH$_3$ | H | H | H |
| T1iii.004 | CH$_2$CH$_3$ | H | H | H |
| T1iii.005 | OCH$_3$ | H | H | H |
| T1iii.006 | Br | Cl | H | H |
| T1iii.007 | Cl | Br | H | H |
| T1iii.008 | Cl | Cl | H | H |

TABLE 1iii-continued

This table discloses the 87 compounds T1iii.001 to T1iii.87 of the subformula (Ic):

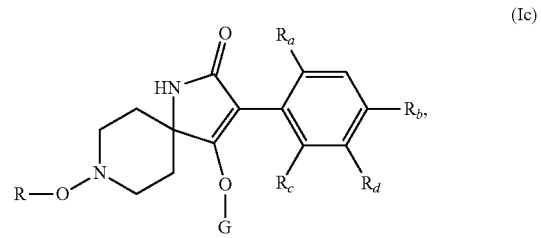

(Ic)

wherein R is CH$_3$, G is —(C=O)—O—CH2CH3 and R$_a$, R$_b$, R$_c$ and R$_d$ are as defined below:

| No. | R$_a$ | R$_b$ | R$_c$ | R$_d$ |
|---|---|---|---|---|
| T1iii.009 | Cl | CH$_3$ | H | H |
| T1iii.010 | CH$_3$ | Cl | H | H |
| T1iii.011 | CH$_3$ | CH$_3$ | H | H |
| T1iii.012 | Cl | H | Cl | H |
| T1iii.013 | Cl | H | CH$_3$ | H |
| T1iii.014 | Cl | H | CH$_2$CH$_3$ | H |
| T1iii.015 | Cl | H | OCH$_3$ | H |
| T1iii.016 | CH$_3$ | H | CH$_3$ | H |
| T1iii.017 | CH$_3$ | H | CH$_2$CH$_3$ | H |
| T1iii.018 | CH$_3$ | H | OCH$_3$ | H |
| T1iii.019 | CH$_2$CH$_3$ | H | CH$_2$CH$_3$ | H |
| T1iii.020 | CH$_2$CH$_3$ | H | OCH$_3$ | H |
| T1iii.021 | OCH$_3$ | H | OCH$_3$ | H |
| T1iii.022 | Br | H | H | Cl |
| T1iii.023 | Br | H | H | CH$_3$ |
| T1iii.024 | Cl | H | H | Cl |
| T1iii.025 | Cl | H | H | CH$_3$ |
| T1iii.026 | CH$_3$ | H | H | Br |
| T1iii.027 | CH$_3$ | H | H | Cl |
| T1iii.028 | CH$_3$ | H | H | CH$_3$ |
| T1iii.029 | CH$_2$CH$_3$ | H | H | CH$_3$ |
| T1iii.030 | OCH$_3$ | H | H | CH$_3$ |
| T1iii.031 | Cl | H | Cl | Br |
| T1iii.032 | CH$_3$ | H | CH$_3$ | Br |
| T1iii.033 | CH$_3$ | H | CH$_3$ | Cl |
| T1iii.034 | Br | Cl | H | CH$_3$ |
| T1iii.035 | Br | CH$_3$ | H | CH$_3$ |
| T1iii.036 | Cl | Cl | H | Cl |
| T1iii.037 | Cl | Br | H | CH$_3$ |
| T1iii.038 | Cl | Cl | H | CH$_3$ |
| T1iii.039 | Cl | CH$_3$ | H | Cl |
| T1iii.040 | Cl | CH$_3$ | H | CH$_3$ |
| T1iii.041 | CH$_3$ | Br | H | CH$_3$ |
| T1iii.042 | CH$_3$ | Cl | H | CH$_3$ |
| T1iii.043 | CH$_3$ | CH$_3$ | H | CH$_3$ |
| T1iii.044 | Br | Br | CH$_3$ | H |
| T1iii.045 | Br | Cl | CH$_3$ | H |
| T1iii.046 | Br | CH$_3$ | Br | H |
| T1iii.047 | Br | CH$_3$ | Cl | H |
| T1iii.048 | Cl | Br | CH$_3$ | H |
| T1iii.049 | Cl | Cl | Cl | H |
| T1iii.050 | Cl | Cl | CH$_3$ | H |
| T1iii.051 | Cl | CH$_3$ | Cl | H |
| T1iii.052 | Cl | CH$_3$ | CH$_2$CH$_3$ | H |
| T1iii.053 | Cl | CH$_3$ | OCH$_3$ | H |
| T1iii.054 | CH$_3$ | Br | CH$_3$ | H |
| T1iii.055 | CH$_3$ | Cl | CH$_3$ | H |
| T1iii.056 | CH$_3$ | CH$_3$ | Br | H |
| T1iii.057 | CH$_3$ | CH$_3$ | Cl | H |
| T1iii.058 | CH$_3$ | CH$_3$ | CH$_3$ | H |
| T1iii.059 | CH$_3$ | CH$_3$ | CH$_2$CH$_3$ | H |
| T1iii.060 | CH$_3$ | CH$_3$ | OCH$_3$ | H |
| T1iii.061 | CH$_2$CH$_3$ | Br | Br | H |
| T1iii.062 | CH$_2$CH$_3$ | Br | Cl | H |
| T1iii.063 | CH$_2$CH$_3$ | Br | CH$_3$ | H |
| T1iii.064 | CH$_2$CH$_3$ | Br | CH$_2$CH$_3$ | H |
| T1iii.065 | CH$_2$CH$_3$ | Br | OCH$_3$ | H |
| T1iii.066 | CH$_2$CH$_3$ | Cl | Br | H |
| T1iii.067 | CH$_2$CH$_3$ | Cl | Cl | H |
| T1iii.068 | CH$_2$CH$_3$ | Cl | CH$_3$ | H |

TABLE 1iii-continued

This table discloses the 87 compounds T1iii.001 to T1iii.87 of the subformula (Ic):

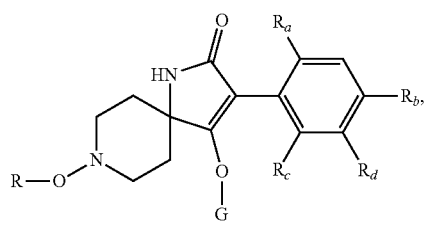
(Ic)

wherein R is $CH_3$, G is —(C=O)—O—CH2CH3 and $R_a$, $R_b$, $R_c$ and $R_d$ are as defined below:

| No. | $R_a$ | $R_b$ | $R_c$ | $R_d$ |
|---|---|---|---|---|
| T1iii.069 | $CH_2CH_3$ | Cl | $CH_2CH_3$ | H |
| T1iii.070 | $CH_2CH_3$ | Cl | $OCH_3$ | H |
| T1iii.071 | $CH_2CH_3$ | $CH_3$ | Br | H |
| T1iii.072 | $CH_2CH_3$ | $CH_3$ | Cl | H |
| T1iii.073 | $CH_2CH_3$ | $CH_3$ | $CH_2CH_3$ | H |
| T1iii.074 | $CH_2CH_3$ | $CH_3$ | $OCH_3$ | H |
| T1iii.075 | $CH_2CH_3$ | $CH_2CH_3$ | $CH_3$ | H |
| T1iii.076 | $CH_2CH_3$ | $CH_2CH_3$ | $CH_2CH_3$ | H |
| T1iii.077 | $OCH_3$ | Br | $CH_3$ | H |
| T1iii.078 | $OCH_3$ | Cl | $CH_3$ | H |
| T1iii.079 | $OCH_3$ | $CH_3$ | Br | H |
| T1iii.080 | $OCH_3$ | $CH_3$ | Cl | H |
| T1iii.081 | $OCH_3$ | $CH_3$ | $OCH_3$ | H |
| T1iii.082 | $CH_3$ | $CH_3$ | $CH_3$ | F |
| T1iii.083 | $CH_3$ | $CH_3$ | $CH_3$ | Cl |
| T1iii.084 | $CH_3$ | $CH_3$ | $CH_3$ | Br |
| T1iii.085 | $CH_3$ | $CH_3$ | $CH_3$ | $CH_3$ |
| T1iii.086 | Cl | CH3 | CH3 | CH3 |
| T1iii.087 | CH3 | Cl | CH3 | CH3 |

Table 2iii: This table discloses the 87 compounds T2iii.001 to T2iii.87 of the formula (Ic), wherein R is $CH_2CH_3$, $R_1$, $R_2$, $R_3$ and $R_4$ are hydrogen, G is —(C=O)—O—CH2CH3 and $R_a$, $R_b$, $R_c$ and $R_d$ are as defined in Table 1iii.

Table 3iii: This table discloses the 87 compounds T3iii.001 to T3iii.87 of the formula (Ic), wherein R is n-$C_3H_7$, $R_1$, $R_2$, $R_3$ and $R_4$ are hydrogen, G is —(C=O)—O—CH2CH3 and $R_a$, $R_b$, $R_c$ and $R_d$ are as defined in Table 1iii.

Table 4iii: This table discloses the 87 compounds T4iii.001 to T4iii.87 of the formula (Ic), wherein R is i-$C_3H_7$, $R_1$, $R_2$, $R_3$ and $R_4$ are hydrogen, G is —(C=O)—O—CH2CH3 and $R_a$, $R_b$, $R_c$ and $R_d$ are as defined in Table 1iii.

Table 5iii: This table discloses the 87 compounds T5iii.001 to T5iii.87 of the formula (Ic), wherein R is hydrogen, $R_1$, $R_2$, $R_3$ and $R_4$ are hydrogen, G is —(C=O)—O—CH2CH3 and $R_a$, $R_b$, $R_c$ and $R_d$ are as defined in Table 1iii.

The compounds of formula (I), including formula (Ia), (Ib) and (Ic), and their manufacturing processes, formulations and adjuvents are known from WO 2009/049851, WO 2010/063670 and WO10/066,780.

The present invention includes all isomers of compounds of formula (I), salts and N-oxides thereof, including enantiomers, diastereomers and tautomers. Component A may be a mixture of any type of isomer of a compound of formula (I), or may be substantially a single type of isomer.

Any one of the above compounds from T1.001 to T44.107, T1ii.001 to T38ii.107 and T1iii. to T5iii.87 can be selected as component A to mix with a component B selected from at least one of the following:

a) Spinosad
b) Pirimicarb
c) Amitraz
d) Buprofezin
e) Pyriproxyfen
f) Triazamate
g) Chlorpyrifos
h) Isoprocarb
i) Indoxacarb
j) Metaflumizone
k) Fipronil
l) Ethiprole
m) Lufenuron
n) Profenofos
o) Oxamyl
p) Bifenthrin
q) Cyfluthrin
r) Deltamethrin
s) Tefluthrin
t) Etoxazole
u) Bifenazate
v) Tau-fluvalinate Preferably, component B is a compound selected from only one of a) to v) above. In other words, preferably the invention provides a two component pesticidal mixture comprising as active ingredient a mixture of component A of formula (I) (including any one of formula (Ia), (Ib) and (Ic)) and component B selected from only one of a) to v).

Preferably, component B is one compound selected from the group consisting of:

a) Spinosad
b) Pirimicarb
c) Amitraz
d) Buprofezin
e) Pyriproxyfen
f) Triazamate
g) Chlorpyrifos
h) Isoprocarb
i) Indoxacarb
j) Metaflumizone
k) Fipronil
l) Ethiprole
m) Lufenuron
n) Profenofos
o) Oxamyl
p) Bifenthrin
q) Cyfluthrin
r) Deltamethrin
s) Tefluthrin
t) Etoxazole
u) Bifenazate
v) Tau-fluvalinate Many sucking pests are known to be vectors of plant diseases caused by microorganisms like bacteria, viruses or phytoplasms. The combination of the compound according to formula (I) for component A and at least one of these compounds for component B has the added advantage of a knock-down effect on various pests that may act as disease vectors, such as for example whiteflies, scales, psyllids, aphids/plant lices and mites. With "knock-down effect", it is meant that the pest to be controlled is rapidly stopped from feeding, quickly totally immobilized or even speedily killed (e.g. at least 80% mortality after 24 hours or 80% mortality after 24 hours), thereby also reducing the risk of infection of the plant exposed to the specified diseases (e.g. viruses)

spread by such pests. Preferably, the active ingredient is a mixture of component A as described above and component B selected from at least one, preferably pirimicarb.

The components B from a) to v) are known, e.g. from "The Pesticide Manual", Fifteenth Edition, Edited by Clive Tomlin, British Crop Protection Council.

Reference to the above components B includes reference to their salts and any usual derivatives, such as ester derivatives and isomers.

It has now been found, surprisingly, that the active ingredient mixture according to the invention not only delivers the additive enhancement of the spectrum of action with respect to the pest to be controlled but achieves a synergistic effect which can extend the range of action of the component A and of the component B in two ways. Firstly, the rates of application of the component A and of the component B are lowered whilst the action remains equally good. Secondly, the active ingredient mixture still achieves a high degree of pest control, sometimes even where the two individual components have become totally ineffective in such a low application rate range. This allows increased safety in use.

However, besides the actual synergistic action with respect to pest control, the pesticidal compositions according to the invention can have further surprising advantageous properties which can also be described, in a wider sense, as synergistic activity. Examples of such advantageous properties that may be mentioned are: a broadening of the spectrum of pest control to other pests, for example to resistant strains; a reduction in the rate of application of the active ingredients; adequate pest control with the aid of the compositions according to the invention, even at a rate of application at which the individual compounds are totally ineffective; advantageous behaviour during formulation and/or upon application, for example upon grinding, sieving, emulsifying, dissolving or dispensing; increased storage stability; improved stability to light; more advantageous degradability; improved toxicological and/or ecotoxicological behaviour; improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination; or any other advantages familiar to a person skilled in the art.

The combinations according to the invention may also comprise more than one of the active components B, if, for example, a broadening of the spectrum of pest control is desired. For instance, it may be advantageous in the agricultural practice to combine two or three components B with any of the compounds of formula (I), or with any preferred member of the group of compounds of formula (I). The mixtures of the invention may also comprise other active ingredients in addition to components A and B.

In other preferred embodiments, the active ingredient is a mixture of only component A and a single active component as component B from the list of a). to v). In other words the pesticidal composition has preferably no more than two pesticidally active components.

Each substituent definition in each preferred group of compounds of formula (I) may be juxtaposed with any substituent definition in any other preferred group of compounds, in any combination.

The weight ratio of A to B is preferably between 1000:1 and 1:100, more preferably between 500:1 and 1:100. In other embodiments that weight ratio of A to B may be between 250:1 to 1:66, for example between 125:1 to 1:33, for example between 100:1 to 1:25, for example between 66:1 to 1:10, for example between 33:1 to 1:5 etc. Such weight ratios lead to synergistic mixtures.

The invention also provides pesticidal mixtures comprising a combination of components A and B as mentioned above in a synergistically effective amount, together with an agriculturally acceptable carrier, and optionally a surfactant.

The following mixtures are particularly favoured for treating plants against pests such as *Myzus persicae* (Green peach aphid) and *Tetranychus urticae* (Two-spotted spider mite), which can be used in the weight ratios mentioned above:

TABLE 45

| | Component A | Component B |
|---|---|---|
| Mixture 1 | T1.055 | Spinosad |
| Mixture 2 | T1.055 | Pirimicarb |
| Mixture 3 | T1.055 | Amitraz |
| Mixture 4 | T1.055 | Buprofezin |
| Mixture 5 | T1.055 | Pyriproxyfen |
| Mixture 6 | T1.055 | Triazamate |
| Mixture 7 | T1.055 | Chlorpyrifos |
| Mixture 8 | T1.055 | Isoprocarb |
| Mixture 9 | T1.055 | Indoxacarb |
| Mixture 10 | T1.055 | Metaflumizone |
| Mixture 11 | T1.055 | Fipronil |
| Mixture 12 | T1.055 | Ethiprole |
| Mixture 13 | T1.055 | Lufenuron |
| Mixture 14 | T1.055 | Profenofos |
| Mixture 15 | T1.055 | Oxamyl |
| Mixture 16 | T1.055 | Bifenthrin |
| Mixture 17 | T1.055 | Cyfluthrin |
| Mixture 18 | T1.055 | Deltamethrin |
| Mixture 19 | T1.055 | Tefluthrin |
| Mixture 20 | T1.055 | Etoxazole |
| Mixture 21 | T1.055 | Bifenazate |
| Mixture 22 | T1.055 | Tau-fluvalinate |
| Mixture 1ii | T1ii.055 | Spinosad |
| Mixture 2ii | T1ii.055 | Pirimicarb |
| Mixture 3ii | T1ii.055 | Amitraz |
| Mixture 4ii | T1ii.055 | Buprofezin |
| Mixture 5ii | T1ii.055 | Pyriproxyfen |
| Mixture 6ii | T1ii.055 | Triazamate |
| Mixture 7ii | T1ii.055 | Chlorpyrifos |
| Mixture 8ii | T1ii.055 | Isoprocarb |
| Mixture 9ii | T1ii.055 | Indoxacarb |
| Mixture 10ii | T1ii.055 | Metaflumizone |
| Mixture 11ii | T1ii.055 | Fipronil |
| Mixture 12ii | T1ii.055 | Ethiprole |
| Mixture 13ii | T1ii.055 | Lufenuron |
| Mixture 14ii | T1ii.055 | Profenofos |
| Mixture 15ii | T1ii.055 | Oxamyl |
| Mixture 16ii | T1ii.055 | Bifenthrin |
| Mixture 17ii | T1ii.055 | Cyfluthrin |
| Mixture 18ii | T1ii.055 | Deltamethrin |
| Mixture 19ii | T1ii.055 | Tefluthrin |
| Mixture 20ii | T1ii.055 | Etoxazole |
| Mixture 21ii | T1ii.055 | Bifenazate |
| Mixture 22ii | T1ii.055 | Tau-fluvalinate |
| Mixture 1iii | T1iii.055 | Spinosad |
| Mixture 2iii | T1iii.055 | Pirimicarb |
| Mixture 3iii | T1iii.055 | Amitraz |
| Mixture 4iii | T1iii.055 | Buprofezin |
| Mixture 5iii | T1iii.055 | Pyriproxyfen |
| Mixture 6iii | T1iii.055 | Triazamate |
| Mixture 7iii | T1iii.055 | Chlorpyrifos |
| Mixture 8iii | T1iii.055 | Isoprocarb |
| Mixture 9iii | T1iii.055 | Indoxacarb |
| Mixture 10iii | T1iii.055 | Metaflumizone |
| Mixture 11iii | T1iii.055 | Fipronil |
| Mixture 12iii | T1iii.055 | Ethiprole |
| Mixture 13iii | T1iii.055 | Lufenuron |
| Mixture 14iii | T1iii.055 | Profenofos |
| Mixture 15iii | T1iii.055 | Oxamyl |
| Mixture 16iii | T1iii.055 | Bifenthrin |

TABLE 45-continued

| | Component A | Component B |
|---|---|---|
| Mixture 17iii | T1iii.055 | Cyfluthrin |
| Mixture 18iii | T1iii.055 | Deltamethrin |
| Mixture 19iii | T1iii.055 | Tefluthrin |
| Mixture 20iii | T1iii.055 | Etoxazole |
| Mixture 21iii | T1iii.055 | Bifenazate |
| Mixture 22iii | T1iii.055 | Tau-fluvalinate |

Preferably, the mixture is Mixture 2, more preferably at a weight ratio of the compound of formula I to pirimicarb of 1:8 to 8:1, even more preferably at a weight ratio of 1:4 to 4:1.

Alternatively, the mixture is Mixture 2iii, more preferably at a weight ratio of the compound of formula I to pirimicarb of 1:64 to 64:1, even more preferably at a weight ratio of 1:8 to 8:1, most preferably 1:4 to 4:1.

The present invention also relates to a method of controlling insects, acarines, nematodes or molluscs which comprises applying to a pest, to a locus of a pest, or to a plant susceptible to attack by a pest a combination of components A and B; seeds comprising a mixture of components A and B; and a method comprising coating a seed with a mixture of components A and B.

Components A and B may be provided and/or used in amounts such that they are capable of synergistic pest control. For example, the present invention includes pesticidal mixtures comprising a component A and a component B in a synergistically effective amount; agricultural compositions comprising a mixture of component A and B in a synergistically effective amount; the use of a mixture of component A and B in a synergistically effective amount for combating animal pests; a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a mixture of component A and B in a synergistically effective amount; a method for protecting crops from attack or infestation by animal pests which comprises contacting a crop with a mixture of component A and B in a synergistically effective amount; a method for the protection of seeds from soil insects and of the seedlings' roots and shoots from soil and foliar insects comprising contacting the seeds before sowing and/or after pre-germination with a mixture of component A and B in a synergistically effective amount; seeds comprising, e.g. coated with, a mixture of component A and B in a synergistically effective amount; a method comprising coating a seed with a mixture of component A and B in a synergistically effective amount; a method of controlling insects, acarines, nematodes or molluscs which comprises applying to a pest, to a locus of a pest, or to a plant susceptible to attack by a pest a combination of components A and B in a synergistically effective amount. Mixtures of A and B will normally be applied in an insecticidally, acaricidally, nematicidally or molluscicidally effective amount. In application components A and B may be applied simultaneously or separately.

The mixtures of the present invention can be used to control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are herein collectively referred to as pests. The pests which may be controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The mixtures of the invention are particularly effective against insects, acarines and/or nematodes. More particularly, the mixtures are effective against hemipterans, acarines and nematodes.

According to the invention "useful plants" with which the mixture according to the invention can be applied, typically comprise the following species of plants: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ACCase inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9c, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). An example for a truncated toxin is a truncated Cry1Ab, which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810)

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9c toxin); Herculex I® (maize variety that expresses a Cry1Fa2 toxin and the enzyme phosphinothricin N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCOT® (cotton variety that expresses a Vip3A and a Cry1Ab toxin); NewLeaf® (potato variety that expresses a Cry3A toxin); NatureGard® and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Useful plants of elevated interest in connection with present invention are cereals; soybean; corn; cotton; rice; oil seed rape; sunflowers; sugarcane; pome fruits; stone fruits; citrus fruits; peanuts, potatoes; coffee; tea; strawberries; turf; vines and vegetables, such as tomatoes, cucurbits and lettuce.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds. Insecticides that are of particular interest for treating seeds include thiamethoxam, imidacloprid and clothianidin.

A further aspect of the instant invention is a method of protecting natural substances of plant and/or animal origin, which have been taken from the natural life cycle, and/or their processed forms against attack of pests, which comprises applying to said natural substances of plant and/or animal origin or their processed forms a combination of components A and B in a synergistically effective amount.

According to the instant invention, the term "natural substances of plant origin, which have been taken from the natural life cycle" denotes plants or parts thereof which have been harvested from the natural life cycle and which are in the freshly harvested form. Examples of such natural substances of plant origin are stalks, leafs, tubers, seeds, fruits or grains. According to the instant invention, the term "processed form of a natural substance of plant origin" is understood to denote a form of a natural substance of plant origin that is the result of a modification process. Such modification processes can be used to transform the natural substance of plant origin in a more storable form of such a substance (a storage good). Examples of such modification processes are pre-drying, moistening, crushing, comminuting, grounding, compressing or roasting. Also falling under the definition of a processed form of a natural substance of plant origin is timber, whether in the form of crude timber, such as construction timber, electricity pylons and barriers, or in the form of finished articles, such as furniture or objects made from wood.

According to the instant invention, the term "natural substances of animal origin, which have been taken from the natural life cycle and/or their processed forms" is understood to denote material of animal origin such as skin, hides, leather, furs, hairs and the like.

A preferred embodiment is a method of protecting natural substances of plant origin, which have been taken from the natural life cycle, and/or their processed forms against attack of pests, which comprises applying to said natural substances of plant and/or animal origin or their processed forms a combination of components A and B in a synergistically effective amount.

A further preferred embodiment is a method of protecting fruits, preferably pomes, stone fruits, soft fruits and citrus fruits, which have been taken from the natural life cycle, and/or their processed forms, which comprises applying to said fruits and/or their processed forms a combination of components A and B in a synergistically effective amount.

The combinations according to the present invention are furthermore particularly effective against the following pests: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Luciffia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus*, *Reticulitermes flavipes*, *R. speratu*, *R. virginicus*, *R. hesperus*, and *R. santonensis*) and the *Termitidae* (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug), *Diaphorina* (psyllids), *Cacopsylla*, *Paratrioza*, and *Brevipalpus* (Leprosis mite).

In another embodiment, the combinations according to the present invention are also particularly effective against the following pests:

from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp,

*Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp., *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp., *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp, *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example,

*Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

The mixtures of the invention may be used for pest control on various plants, including soybean, alfalfa, brassicas (e.g. broccoli, cabbage, cauliflower), or oil crops, such as oilseed rape, mustard, canola, poppies, olives, sunflowers, coconut, castor, cocoa or ground nuts, or potatoes (including sweet potatoes), almonds, fruiting vegetables (e.g. tomatoes, pepper, chili, eggplant, etc.), leafy vegetables (lettuce, spinach), bulb vegetables (e.g. onion, leek etc.), grapes, fruit, for instance pomaceous fruit, stone fruit or soft fruit (e.g. apples, pears, plums, peaches, nectarines, almonds, cherries etc.) or berries, for example strawberries, raspberries or blackberries.

Other suitable target crops are, in particular, cereals, such as wheat, barley, rye, oats, rice, maize or sorghum; beet, such as sugar or fodder beet; leguminous crops, such as beans, lentils, peas, peanuts or soya; cucurbits, such as pumpkins, cucumbers, squash or melons; fibre plants, such as cotton, flax, hemp or jute; citrus fruit, such as oranges, lemons, grapefruit or tangerines; vegetables, such as spinach, lettuce, asparagus, cabbages, carrots, onions, or bell peppers; Lauraceae, such as avocado, Cinnamonium or camphor; and also tobacco, nuts (e.g. pecan nuts, walnut), coffee, sugarcane, tea, pepper, grapevines, tropical fruits (e.g. papaya, mango), hops, the plantain family, latex plants and ornamentals. The mixtures of the invention can also be applied on turf, lawn and pastures.

The mixtures of the invention may be used on soybean to control, for example, *Elasmopalpus lignosellus, Diloboderus abderus, Diabrotica speciosa, Sternechus subsignatus, Formicidae, Agrotis ypsilon, Julus* sspp., *Anticarsia gemmatalis, Megascelis* ssp., *Procornitermes* ssp., *Gryllotalpidae, Nezara viridula, Piezodorus* spp., *Acrosternum* spp., *Neomegalotomus* spp., *Cerotoma trifurcata, Popillia japonica, Edessa* spp., *Liogenys fuscus, Euchistus heros*, stalk borer, *Scaptocoris castanea, phyllophaga* spp., *Pseudoplusia includens, Spodoptera* spp., *Bemisia tabaci, Agriotes* spp. *Aphis* sp (e.g. *Aphis glycines*). The mixtures of the invention are preferably used on soybean to control *Diloboderus abderus, Diabrotica speciosa, Nezara viridula, Piezodorus* spp., *Acrosternum* spp., *Cerotoma trifurcata, Popillia japonica, Euchistus heros, phyllophaga* spp., *Agriotes* sp, *Aphis* sp (e.g. *Aphis glycines*)

The mixtures of the invention may be used on corn to control, for example, *Euchistus heros, Dichelops furcatus, Diloboderus abderus, Elasmopalpus lignosellus, Spodoptera frugiperda, Nezara viridula, Cerotoma trifurcata, Popillia japonica, Agrotis ypsilon, Diabrotica speciosa, Heteroptera, Procornitermes* ssp., *Scaptocoris castanea, Formicidae, Julus* ssp., *Dalbulus maidis, Diabrotica virgifera, Mocis latipes, Bemisia tabaci, heliothis* spp., *Tetranychus* spp., *thrips* spp., *phyllophaga* spp., *scaptocoris* spp., *Liogenys fuscus, Spodoptera* spp., *Ostrinia* spp., *Sesamia* spp., *Agriotes* spp., *Aphis* sp. The mixtures of the invention are preferably used on corn to control *Euchistus heros, Dichelops furcatus, Diloboderus abderus, Nezara viridula, Cerotoma trifurcata, Popillia japonica, Diabrotica speciosa, Diabrotica virgifera, Tetranychus* spp., *thrips* spp., *phyllophaga* spp., *scaptocoris* spp., *Agriotes* spp., *Aphis* sp The mixtures of the invention may be used on sugar cane to control, for example, *Sphenophorus* spp., termites, *Mahanarva* spp. The mixtures of the invention are preferably used on sugar cane to control termites, *Mahanarva* spp.

The mixtures of the invention may be used on alfalfa to control, for example, *Hypera brunneipennis, Hypera postica, Colias eurytheme, Collops* spp., *Empoasca solana, Epitrix, Geocoris* spp., *Lygus hesperus, Lygus lineolaris, Spissistilus* spp., *Spodoptera* spp., *Trichoplusia ni*. The mixtures of the invention are preferably used on alfalfa to control *Hypera brunneipennis, Hypera postica, Empoasca solana, Epitrix, Lygus hesperus, Lygus lineolaris, Trichoplusia ni.*

The mixtures of the invention may be used on brassicas to control, for example, *Plutella xylostella, Pieris* spp., *Mamestra* spp., *Plusia* spp., *Trichoplusia ni, Phyllotreta* spp., *Spodoptera* spp., *Empoasca solana, thrips* spp., *Spodoptera* spp., *Delia* spp. *Brevicoryne* sp, *Macrosiphum* sp. The mixtures of the invention are preferably used on brassicas to control *Plutella xylostella Pieris* spp., *Plusia* spp., *Trichoplusia ni, Phyllotreta* spp., *thrips* sp The mixtures of the invention may be used on oil seed rape, e.g. canola, to control, for example, *Meligethes* spp., *Ceutorhynchus napi, Psylloides* spp.

The mixtures of the invention may be used on potatoes, including sweet potatoes, to control, for example, *Empoasca* spp., *Leptinotarsa* spp., *Diabrotica speciosa, Phthorimaea* spp., *Paratrioza* spp., *Maladera matrida, Agriotes* spp., *Bemisia* sp, *Myzus* sp., *Macrosiphum* sp. *Aphis* sp, *Aulacorthum* sp. *Rhopalosiphum* sp. The mixtures of the invention are preferably used on potatoes, including sweet potatoes, to control *Empoasca* spp., *Leptinotarsa* spp., *Diabrotica speciosa, Phthorimaea* spp., *Paratrioza* spp., *Agriotes* spp, *Bemisia* sp, *Myzus* sp., *Macrosiphum* sp. *Aphis* sp, *Aulacorthum* sp. *Rhopalosiphum* sp.

The mixtures of the invention may be used on cotton to control, for example, *Aphis gossypii, Anthonomus grandis, Pectinophora* spp., *heliothis* spp., *Spodoptera* spp., *Tetranychus* spp., *Empoasca* spp., *thrips* spp., *Bemisia tabaci, Lygus* spp., *phyllophaga* spp., *Scaptocoris* spp. The mixtures of the invention are preferably used on cotton to control *Aphis gossypii, Anthonomus grandis, Tetranychus* spp., *Empoasca* spp., *thrips* spp., *Lygus* spp., *phyllophaga* spp., *Scaptocoris* spp.

The mixtures of the invention may be used on rice to control, for example, *Nilaparvata lugens, Leptocorisa* spp., *Cnaphalocrosis* spp., *Chilo* spp., *Scirpophaga* spp., *Lissorhoptrus* spp., *Oebalus pugnax*. The mixtures of the invention are preferably used on rice to control *Nilaparvata lugens, Leptocorisa* spp., *Lissorhoptrus* spp., *Oebalus pugnax.*

The mixtures of the invention may be used on coffee to control, for example, *Brevipalpus* sp, *Hypothenemus Hampei, Perileucoptera Coffeella, Tetranychus* spp. The mixtures of the invention are preferably used on coffee to control *Hypothenemus Hampei, Perileucoptera Coffeella, Brevipalpus* sp, The mixtures of the invention may be used on citrus to control, for example, *Panonychus citri, Phyllocoptruta oleivora, Brevipalpus* spp., *Diaphorina citri, Scirtothrips* spp., *thrips* spp., *Unaspis* spp., *Ceratitis capitata, Phyllocnistis* spp., *Brevipalpus* sp. *Aonidiella* sp, *Parlatoria* sp, *Ceroplastes* sp, *Planococcus* sp, *Pseudococcus* sp., *Tet-* ranychus sp. *Aphis* sp. The mixtures of the invention are preferably used on citrus to control *Panonychus citri, Phyllocoptruta oleivora, Brevipalpus* spp., *Diaphorina citri, Scirtothrips* spp., *thrips* spp., *Phyllocnistis* spp, *Brevipalpus* sp. *Aonidiella* sp, *Parlatoria* sp, *Ceroplastes* sp, *Planococcus* sp, *Pseudococcus* sp., *Tetranychus* sp., *Aphis* sp.

The mixtures of the invention may be used on almonds to control, for example, *Amyelois transitella, Tetranychus* spp.

The mixtures of the invention may be used on fruiting vegetable, including tomatoes, pepper, chili, eggplant, cucumber, squash etc, to control *Myzus* sp, *Aphis* sp, *thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Bemisia tabaci, Trialeurodes* spp., *Paratrioza* spp., *Frankliniella occidentalis, Frankliniella* spp., *Anthonomus* spp., *Phyllotreta* spp., *Amrasca* spp., *Epilachna* spp., *Halyomorpha* spp., *Scirtothrips* spp., *Leucinodes* spp., *Neoleucinodes* spp. The mixtures of the invention are preferably used on fruiting vegetable, including tomatoes, pepper, chili, eggplant, cucumber, squash etc, to control, for example, *Myzus* sp, *Aphis* sp, *thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Paratrioza* spp., *Frankliniella occidentalis, Frankliniella* spp., *Amrasca* spp., *Scirtothrips* spp., *Leucinodes* spp., *Neoleucinodes* spp.

The mixtures of the invention may be used on tea to control, for example, *Pseudaulacaspis* spp., *Empoasca* spp., *Scirtothrips* spp., *Caloptilia theivora*. The mixtures of the invention are preferably used on tea to control *Empoasca* spp., *Scirtothrips* spp.

The mixtures of the invention may be used on bulb vegetables, including onion, leek etc to control, for example, *thrips* spp., *Spodoptera* spp., *heliothis* spp. The mixtures of the invention are preferably used on bulb vegetables, including onion, leek etc to control *thrips* spp.

The mixtures of the invention may be used on grapes to control, for example, *Empoasca* spp., *Lobesia* spp., *Frankliniella* spp., *thrips* spp., *Tetranychus* spp., *Rhipiphorothrips Cruentatus, Eotetranychus Willamettei, Erythroneura Elegantula, Scaphoides* spp, *Pseudococcus* sp, *Planococcus* sp The mixtures of the invention are preferably used on grapes to control *Frankliniella* spp., *thrips* spp., *Tetranychus* spp., *Rhipiphorothrips Cruentatus, Scaphoides* spp, *Pseudococcus* sp, *Planococcus* sp The mixtures of the invention may be used on pome fruit, including apples, pairs etc, to control, for example, *Cacopsylla* spp., *Psylla* spp., *Panonychus ulmi, Cydia pomonella, Quadraspidiotus* sp, *Lepidosaphes* sp, *Aphis* sp, *Dysaphis* sp, *Eriosoma* sp. The mixtures of the invention are preferably used on pome fruit, including apples, pairs etc, to control *Cacopsylla* spp., *Psylla* spp., *Panonychus ulmi Quadraspidiotus* sp, *Lepidosaphes* sp, *Aphis* sp, *Dysaphis* sp, *Eriosoma* sp The mixtures of the invention may be used on stone fruit to control, for example, *Grapholita molesta, Scirtothrips* spp., *thrips* spp., *Frankliniella* spp., *Tetranychus* spp., *Myzus* sp. The mixtures of the invention are preferably used on stone fruit to control *Scirtothrips* spp., *thrips* spp., *Frankliniella* spp., *Tetranychus* spp., *Myzus* sp. The amount of a combination of the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of pest to be controlled or the application time.

The invention also provides mixtures suitable for resistance management. In particular, the mixtures according to the invention are suitable for controlling insects, for example from the Hemiptera order such as aphids (e.g. *Myzus* spp), which are resistant to neonicotinoid insecticides. The method comprises applying to said neonicotinoid resistant insects a mixture according to the invention.

The mixtures of the invention are particularly applicable to the control of neonicotinoid resistant insects (and neonicotinoid resistance in insects) of the order Hemiptera, such as: *Acyrthosiphum pisum, Aphis citricola, Aphis craccivora, Aphis fabae, Aphis frangulae, Aphis glycines, Aphis gossypii, Aphis nasturtii, Aphis pomi, Aphis spiraecola, Aulacorthum solani, Brachycaudus helichrysi, Brevicoryne brassicae, Diuraphis noxia, Dysaphis devecta, Dysaphis plantaginea, Eriosoma lanigerum, Hyalopterus pruni, Lipaphis erysimi, Macrosiphum avenae, Macrosiphum euphorbiae, Macrosiphum rosae, Myzus cerasi* F., *Myzus nicotianae, Myzus persicae, Nasonovia ribisnigri, Pemphigus bursarius, Phorodon humuli, Rhopalosiphum insertum* Wa, *Rhopalosiphum maidis* Fitch, *Rhopalosiphum padi* L., *Schizaphis graminum* Rond., *Sitobion avenae, Toxoptera aurantii, Toxoptera citricola, Phylloxera vitifoliae, Acyrthosiphon dirhodum, Acyrthosiphon solani, Aphis forbesi, Aphis grossulariae, Aphis idaei, Aphis illinoisensis, Aphis maidiradicis, Aphis ruborum, Aphis schneideri, Brachycaudus persicaecola, Cavariella aegopodii* Scop., *Cryptomyzus galeopsidis, Cryptomyzus ribis, Hyadaphis pseudobrassicae, Hyalopterus amygdali, Hyperomyzus pallidus, Macrosiphoniella sanborni, Metopolophium dirhodum, Myzus malisuctus, Myzus varians, Neotoxoptera* sp, *Nippolachnus piri* Mats., *Oregma lanigera* Zehnter, *Rhopalosiphum fitchii* Sand., *Rhopalosiphum nymphaeae, Rhopalosiphum sacchari* Ze, *Sappaphis piricola* Okam.+T, *Schizaphis piricola, Toxoptera theobromae* Sch, and *Phylloxera coccinea,*

*Aleurodicus dispersus, Aleurocanthus spiniferus, Aleurocanthus woglumi, Aleurodicus cocois, Aleurodicus destructor, Aleurolobus barodensis, Aleurothrixus floccosus, Bemisia tabaci, Bemisia argentifolli, Dialeurodes citri, Dialeurodes citrifolli, Parabemisia myricae, Trialeurodes packardi, Trialeurodes ricini, Trialeurodes vaporariorum, Trialeurodes variabilis,*

*Agonoscena targionii, Bactericera cockerelli, Cacopsylla pyri, Cacopsylla pyricola, Cacopsylla pyrisuga, Diaphorina citri, Glycaspis brimblecombei, Paratrioza cockerelli, Troza erytreae,*

*Amarasca biguttula biguttula, Amritodus atkinsoni, Cicadella viridis, Cicadulina mbila, Cofana spectra, Dalbulus maidis, Empoasca decedens, Empoasca biguttula, Empoasca fabae, Empoasca vitis, Empoasca papaya, Idioscopus clypealis, Jacobiasca lybica, Laodelphax striatellus, Myndus crudus, Nephotettix virescens, Nephotettix cincticeps, Nilaparvata lugens, Peregrinus maidis, Perkinsiella saccharicida, Perkinsiella vastatrix, Recilia dorsalis, Sogatella furcifera, Tarophagus Proserpina, Zygina flammigera,*

*Acanthocoris scabrator, Adelphocoris lineolatus, Amblypelta nitida, Bathycoelia thalassina, Blissus leucopterus, Clavigralla tomentosicollis, Edessa meditabunda, Eurydema pulchrum, Eurydema rugosum, Eurygaster Maura, Euschistus servus, Euschistus tristigmus, Euschistus heros Helopeltis antonii, Horcias nobilellus, Leptocorisa acuta, Lygus lineolaris, Lygus hesperus, Murgantia histrionic, Nesidiocoris tenuis, Nezara viridula, Oebalus insularis, Scotinophara coarctata,*

Specific examples of neonicotinoid resistant Hemiptera include *Bemisia tabaci, Myzus persicae, Nilaparvata lugens, Aphis gossypii, Trialeurodes vaporariorum, Bactericera cockerelli*.

Preferably, the neonicotinoid resistant insects are one or more of as an example *Acyrthosiphum pisum, Aphis citricola, Aphis craccivora, Aphis fabae, Aphis frangulae, Aphis glycines, Aphis gossypii, Aphis nasturtii, Aphis pomi, Aphis spiraecola, Aulacorthum solani, Brachycaudus helichrysi, Brevicoryne brassicae, Diuraphis noxia, Dysaphis devecta, Dysaphis plantaginea, Eriosoma lanigerum, Hyalopterus pruni, Lipaphis erysimi, Macrosiphum avenae, Macrosiphum euphorbiae, Macrosiphum rosae, Myzus cerasi* F., *Myzus nicotianae, Myzus persicae, Nasonovia ribisnigri, Pemphigus bursarius, Phorodon humuli, Rhopalosiphum insertum* Wa, *Rhopalosiphum maidis* Fitch, *Rhopalosiphum padi* L., *Schizaphis graminum* Rond., *Sitobion avenae, Toxoptera aurantii, Toxoptera citricola, Phylloxera vitifoliae, Bemisia tabaci, Myzus persicae, Nilaparvata lugens, Aphis gossypii, Trialeurodes vaporariorum, Bactericera cockerelli*.

More preferably, the neonicotinoid resistant insects are one or more of as an example *Bemisia tabaci, Myzus persicae, Nilaparvata lugens, Aphis gossypii, Trialeurodes vaporariorum, Bactericera cockerelli*.

The mixtures comprising a compound of formula (I), e.g. those selected from the tables above, and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) e.g. those selected from the tables above and the active ingredients as described above is not essential for working the present invention.

The synergistic activity of the combination is apparent from the fact that the pesticidal activity of the composition of A+B is greater than the sum of the pesticidal activities of A and B.

The method of the invention comprises applying to the useful plants, the locus thereof or propagation material thereof in admixture or separately, a synergistically effective aggregate amount of a component A and a component B.

Some of said combinations according to the invention have a systemic action and can be used as foliar, soil and seed treatment pesticides. The invention also covers a a method comprising coating a seed with a mixture of components A and B as defined above.

With the combinations according to the invention it is possible to inhibit or destroy the pests which occur in plants or in parts of plants (fruit, blossoms, leaves, stems, tubers, roots) in different useful plants, while at the same time the parts of plants which grow later are also protected from attack by pests.

The combinations of the present invention are of particular interest for controlling pests in various useful plants or their seeds, especially in field crops such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and cucurbits.

The combinations according to the invention are applied by treating the pests, the useful plants, the locus thereof, the propagation material thereof, the natural substances of plant and/or animal origin, which have been taken from the natural life cycle, and/or their processed forms, or the industrial materials threatened by pests, attack with a combination of components A and B in a synergistically effective amount.

The combinations according to the invention may be applied before or after infection or contamination of the useful plants, the propagation material thereof, the natural substances of plant and/or animal origin, which have been taken from the natural life cycle, and/or their processed forms, or the industrial materials by the pests.

The combinations according to the invention can be used for controlling, i.e. containing or destroying, pests of the abovementioned type which occur on useful plants in agriculture, in horticulture and in forests, or on organs of useful plants, such as fruits, flowers, foliage, stalks, tubers or roots, and in some cases even on organs of useful plants which are formed at a later point in time remain protected against these pests.

When applied to the useful plants the compound of formula (I) is generally applied at a rate of 1 to 500 g a.i./ha in association with 1 to 2000 g a.i./ha, of a compound of component B, depending on the class of chemical employed as component B.

Generally for plant propagation material, such as seed treatment, application rates can vary from 0.001 to 10 g/kg of seeds of active ingredients. When the combinations of the present invention are used for treating seed, rates of 0.001 to 5 g of a compound of formula (I) per kg of seed, preferably from 0.01 to 1 g per kg of seed, and 0.001 to 5 g of a compound of component B, per kg of seed, preferably from 0.01 to 1 g per kg of seed, are generally sufficient.

*Spodoptera* preferably means *Spodoptera littoralis*. *Heliothis* preferably means *Heliothis virescens*. *Tetranychus* preferably means *Tetranychus urticae*.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

The compositions according to the invention can preferably additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil such as ADIGOR® and MERO®, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Also, alkoxylated fatty acids can be used as additives in the inventive compositions as well as polymethylsiloxane based additives, which have been described in WO08/037,373.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyloxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pen-e-trate®, can also be mixed into the spray mixture as activity-enhancing agents.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules. A typical a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation. A typical pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with a compound of component B, and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms the synergism factor SF corresponds to O/E. In the agricultural practice an SF of ≥1.2 indicates significant improvement over the purely complementary addition of activities (expected activity), while an SF of ≤0.9 in the practical application routine signals a loss of activity compared to the expected activity.

Table 45 shows mixtures of T1.055, T1ii.055 and T1iii.055 and a Component B of the present invention to be used for demonstrating control on a wide range of pests. As the percent of mortality cannot exceed 100 percent, the unexpected increase in insecticidal activity can be greatest only when the separate active ingredient components alone are at application rates providing considerably less than 100 percent control. Synergy may not be evident at low application rates where the individual active ingredient components alone have little activity. However, in some instances high activity can be observed for combinations wherein individual active ingredient alone at the same application rate have essentially no activity.

*Myzus persicae* (Green Peach Aphid):
feeding/residual contact activity, preventive Sunflower leaf discs were placed on agar in a 24-well microtiter plate and sprayed with the DMSO test solutions of Mixtures (as provided by Table 45). After drying, the leaf discs were infested with an aphid population of mixed ages. After an incubation period of 6 DAT (days after treatment), samples were checked for mortality. (1 PPM=1 mg l$^{-1}$) Results are shown in Table 46 and Table 47.

TABLE 46

| PPM AI | | AVERAGE DEAD IN % AFTER 6 DAYS | | EXPECTED MORTALITY | OBSERVED MORTALITY |
|---|---|---|---|---|---|
| T1.055 | Pirimicarb | T1.055 | Pirimicarb | | |
| 50 | 12.5 | 0 | 0 | 0 | 15* |
| 50 | 25 | 0 | 17.5 | 17.5 | 50* |
| 50 | 50 | 0 | 65 | 65 | 50 |
| 50 | 100 | 0 | 87.5 | 87.5 | 95* |
| 50 | 200 | 0 | 100 | 100 | 100 |

TABLE 47

| PPM AI | | AVERAGE DEAD IN % AFTER 6 DAYS | | EXPECTED MORTALITY | OBSERVED MORTALITY |
|---|---|---|---|---|---|
| T1iii.055 | Pirimicarb | T1iii.055 | Pirimicarb | | |
| 100 | 25 | 90 | 17.5 | 91.75 | 100* |
| 50 | 25 | 70 | 17.5 | 75.25 | 85* |
| 25 | 25 | 30 | 17.5 | 42.25 | 90* |

TABLE 47-continued

| PPM AI | | AVERAGE DEAD IN % AFTER 6 DAYS | | EXPECTED MORTALITY | OBSERVED MORTALITY |
|---|---|---|---|---|---|
| T1iii.055 | Pirimicarb | T1iii.055 | Pirimicarb | | |
| 12.5 | 25 | 0 | 17.5 | 17.5 | 95* |
| 6.25 | 25 | 0 | 17.5 | 17.5 | 30* |

*Tetranychus urticae* (Two-Spotted Spider Mite):
feeding/contact activity, preventive Bean leaf discs on agar in 24-well microtiter plates were sprayed with the DMSO test solutions of certain Mixtures (as provided by Table 45). After drying, the leaf discs were infested with mite populations of mixed ages. 8 days later, discs were checked for mortality against mobile stages. (1 PPM=1 mg l$^{-1}$) Results are shown in Table 48 and 49.

TABLE 48

| PPM AI | | AVERAGE DEAD IN % AFTER 8 DAYS | | EXPECTED MORTALITY | OBSERVED MORTALITY |
|---|---|---|---|---|---|
| T1.055 | Pirimicarb | T1.055 | Pirimicarb | | |
| 800 | 200 | 90 | 0 | 90 | 95* |
| 400 | 200 | 85 | 0 | 85 | 90* |
| 200 | 200 | 65 | 0 | 65 | 75* |
| 100 | 200 | 45 | 0 | 45 | 75* |
| 50 | 200 | 0 | 0 | 0 | 65* |

TABLE 49

| PPM AI | | AVERAGE DEAD IN % AFTER 8 DAYS | | EXPECTED MORTALITY | OBSERVED MORTALITY |
|---|---|---|---|---|---|
| T1iii.055 | Pirimicarb | T1iii.055 | Pirimicarb | | |
| 6.25 | 25 | 0 | 0 | 0 | 0 |
| 6.25 | 50 | 0 | 0 | 0 | 15* |
| 6.25 | 100 | 0 | 0 | 0 | 25* |
| 6.25 | 200 | 0 | 0 | 0 | 35* |
| 6.25 | 400 | 0 | 0 | 0 | 35* |

The invention claimed is:

1. A pesticidal mixture comprising as active ingredient a mixture of component A and component B, wherein component A is a compound of formula (I)

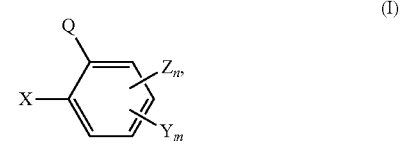

in which Q is

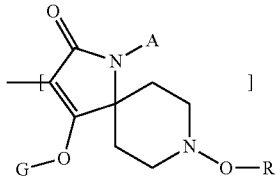

wherein
m is 1, n is 1, X is methyl, Y is in the ortho position and is methyl, Z is in the para position and is chloro, G is —(C═O)O—CH$_2$CH$_3$, A is methyl and R is methyl; or m is 1, n is 1, X is methyl, Y is in the ortho position and is methyl, Z is in the para position and is chloro, G is —(C═O)O—CH$_2$CH$_3$, A is hydrogen and R is methyl;

or an agrochemically acceptable salt or an N-oxide thereof;
and component B is pirimicarb; and
wherein the weight ratio of component (A) to component (B) is from 4:1 to 1:4.

2. A pesticidal mixture according to claim 1, wherein the mixture comprises an agricultural acceptable carrier and optionally a surfactant.

3. A pesticidal mixture according to claim 1, wherein the mixture comprises formulation adjuvants.

4. A seed comprising a mixture as defined in claim 1.

5. A method of controlling insects or acarines, which comprises applying to a pest, to a locus of a pest, or to a plant susceptible to attack by a pest a combination of components A and B, wherein components A and B are a mixture as defined in claim 1.

6. The method according to claim 5 wherein the mixture further comprises an agricultural acceptable carrier.

7. The method according to claim 5 for controlling insects, wherein the insects are neonicotinoid resistant.

* * * * *